United States Patent
Zalis et al.

(10) Patent No.: US 10,541,054 B2
(45) Date of Patent: Jan. 21, 2020

(54) STRUCTURED SUPPORT OF CLINICAL HEALTHCARE PROFESSIONALS

(71) Applicants: Michael E. Zalis, Newtonville, MA (US); Mitchell A. Harris, West Newton, MA (US); Creagh Milford, Boston, MA (US); Timothy Ferris, Boston, MA (US)

(72) Inventors: Michael E. Zalis, Newtonville, MA (US); Mitchell A. Harris, West Newton, MA (US); Creagh Milford, Boston, MA (US); Timothy Ferris, Boston, MA (US)

(73) Assignee: Massachusetts General Physicians Organization, Boston, MA (US)

( * ) Notice: Subject to any disclaimer, the term of this patent is extended or adjusted under 35 U.S.C. 154(b) by 551 days.

(21) Appl. No.: 14/912,976

(22) PCT Filed: Aug. 19, 2014

(86) PCT No.: PCT/US2014/051652
§ 371 (c)(1),
(2) Date: Feb. 19, 2016

(87) PCT Pub. No.: WO2015/026799
PCT Pub. Date: Feb. 26, 2015

(65) Prior Publication Data
US 2016/0203281 A1    Jul. 14, 2016

Related U.S. Application Data

(60) Provisional application No. 61/867,497, filed on Aug. 19, 2013.

(51) Int. Cl.
*G16H 50/20* (2018.01)
*G06Q 50/24* (2012.01)
(Continued)

(52) U.S. Cl.
CPC ............. *G16H 50/20* (2018.01); *G16H 10/60* (2018.01); *G16H 15/00* (2018.01); *G16H 40/20* (2018.01); *G16H 50/30* (2018.01); *G16H 50/70* (2018.01)

(58) Field of Classification Search
CPC ........ G06Q 50/22; G16H 10/60; G16H 50/20; G16H 50/70; G16H 50/30;
(Continued)

(56) References Cited

U.S. PATENT DOCUMENTS 7,395,511 B1    7/2008    Robertson et al.
7,899,764 B2    3/2011    Martin et al.
(Continued)

OTHER PUBLICATIONS

International Search Report and Written Opinion dated Dec. 9, 2014 in connection with PCT/US2014/051652.
(Continued)

*Primary Examiner* — Robert A Sorey
*Assistant Examiner* — Kristine K Rapillo
(74) *Attorney, Agent, or Firm* — Quarles & Brady LLP

(57) ABSTRACT

A system and method is provided for using a communications network coupling a plurality of computer systems, a database, and a at least one external data source together to facilitate communication therebetween. The plurality of computer systems is configured to extract at least one term from a medical order for the patient, identify at least one medical concept related to an extracted term, and identify at least one medical data element related to an identified medical concept. The plurality of computer system is further configured to query the database for the identified at least one medical data element, query the at least one external data source to retrieve at least one guideline for performing at least one intervention associated with the at least one (Continued)

medical data element, and generate a user interface that displays at least a portion of a result from the queries.

20 Claims, 15 Drawing Sheets

(51) Int. Cl.
*G06F 19/00* (2018.01)
*G16H 10/60* (2018.01)
*G16H 40/20* (2018.01)
*G16H 50/30* (2018.01)
*G16H 50/70* (2018.01)
*G16H 15/00* (2018.01)
*G16C 99/00* (2019.01)

(58) Field of Classification Search
CPC .......... G06F 16/24578; G06F 16/9024; G06F 16/285; G06F 16/95; G06F 16/93; G06F 17/2785
See application file for complete search history.

(56) References Cited

U.S. PATENT DOCUMENTS

| | | | |
|---|---|---|---|
| 2009/0299977 A1 | 12/2009 | Rosales | |
| 2010/0281025 A1* | 11/2010 | Tsatsou | G06F 16/335 707/733 |
| 2011/0046979 A1* | 2/2011 | Tulipano | G06F 19/325 705/2 |
| 2011/0129131 A1* | 6/2011 | Avinash | G16H 50/20 382/128 |
| 2013/0035961 A1* | 2/2013 | Yegnanarayanan | G16H 10/60 705/3 |
| 2013/0103414 A1 | 4/2013 | Eng | |

OTHER PUBLICATIONS

Lin, et al., Initial Observations of Electronic Medical Record Usage During CT and MRI Interpretation: Frequency of Use and Impact on Workflow, American Journal of Roentgenology, 2010, 195(1):188-193.
European Patent Office, Extended European Search Report, Application No. 14837789.8, dated Mar. 31, 2017.

* cited by examiner

FIG. 4

| | | | | | | |
|---|---|---|---|---|---|---|
| QPID PrOE | MRN: 0000002 | Visit Date: 2013-08-02 | Go Refresh | | Options Legend Feedback Help | |
| Long, Alvan (0000002) 107 /M | | Visit Date: 2013-08-02 Selected Intervention: TKA-Left | | | Risks completed | |

Intervention | Clinical Summary | Guidelines | Risks | Assessment | Consent | Schedule

Start New Evaluation — Continue Saved Evaluation for MRN 0000002

Vascular:
- ○ CEA
- ○ CAS
- ○ Medical Therapy Only

Cardiac:
- ○ CABG
- ○ PCI
- ▶ Diagnostic Catheterization
  - ○ Known ACS
  - ○ Known obstructive CAD
  - ○ Suspected CAD
  - ○ Preoperative evaluation
  - ○ Cardiomyopathy
  - ○ Valvular Disease
  - ○ Pericardial disease
  - ○ Arrhythmia
  - ○ Newly diagnosed LBBB

| Intervention | Visit Date | Started By | Evaluation Status | Score | Last Updated On | Updated By |
|---|---|---|---|---|---|---|
| CAS | 2013-08-16 | cm119 | Intervention confirmed. | 8 | 08-16-2013 at 12:07:59 | cm119 |
| CEA (Left) | 2012-12-04 | sg676 | No edits yet. | | 08-12-2013 at 11:39:56 | sg676 |
| Suspected CAD | 2103-08-12 | cm119 | Assessment completed. | | 08-12-2013 at 07:31:34 | cm119 |
| Arrhythmia | 2013-08-02 | nj098 | Intervention confirmed. | 5 | 08-09-2013 at 09:11:28 | nj098 |
| Suspected CAD | 2013-08-02 | nj098 | Intervention confirmed. | 4 | 08-08-2013 at 23:56:07 | nj098 |
| CABG (Left) | 2013-08-02 | mah80 | No edits yet. | | 08-07-2013 at 17:43:14 | mah80 |
| TKA (Left) | 2013-08-02 | mah80 | Risks completed. | | 08-07-2013 at 17:35:16 | mah80 |
| Arrhythmia | 2013-08-02 | mah80 | Risks completed. | | 08-07-2013 at 17:18:44 | mah80 |
| Suspected | 2013-08-02 | mah80 | Risks | | 08-07-2013 | mah80 |

◀ 1-10 of 96 ◉ ⊗

Next – Summary>

| QPID ProE | | Refresh | | Options Legend Feedback Help |
|---|---|---|---|---|
| Test, Ignore (0000006) 40 /M Visit Date: 2012-12-04 Selected Intervention: CEA-Left | | | | Edit Assessment  Intervention confirmed |

Intervention | Clinical Summary | Guidelines | Risks | Assessment | Consent | Schedule

Selected Labs
- PLT 299 2010-06-17
- PT-INR 2.2 2011-03-18
- PTT Credit 2012-08-14
- Na 140 2007-09-03
- K 2.2 2007-09-03
- Ca 4.3 2007-09-03
- BUN 40 2007-09-03
- Cr 1.25 2008-02-15
- eGFR Estimated 2008-02-15
- WBC 5.9 2010-06-17
- HCT 39.1 2010-06-17
- Hgb 13.2 2010-06-17
- HIT 0.3 2007-09-03
- Bili-T 1.8 2007-09-03
- Albumin
- Hgb A1C
- HDL
- LDL
- Triglycerides
- ESR 13 2003-10-30

Recent Reports
- Past Med History
- Advance Directives
- All Medications
- Antibotics
- Anticoagulants

Notes
- LMR Notes
- Endoscopy Notes
- OP Notes
- Bad Reports

Selected Searches
- Oxygen dependent
- Allergies
- EF less than 40
- AICD / Peacemaker
- PFO DIS 01/09/2010 Discharge Summary Sleep Apnea

Diagnostic Studies
- Echo
- Ultrasound
- Cerebral Arteriogram
- ECG    510
- CT
- CTA
- MRI
- MRA

Selected Problems
- Aortic Aneurysm / Dissection
- Carotid Stent
- External Stenosis
- High Carotid Bulb    512
- Previous CEA
- Restenosis In CAS
- Transient Ischemic Attack
- Cardiovasular Disease 1 result for *VIR_PRO
...r function with pulmonary pressures 3/4 systemic, PFO with bidirectional flow, email left pulmonary artery with difficul...

504    506    508

500
502
514

<Back – Intervention    Save    Next – Guidelines>

| QPID PrOE | | | | | | Options Legend Feedback Help |
|---|---|---|---|---|---|---|
| ☐ Test, Ignore (0000006) 40 / M Visit Date: 2012-12-04 [Refresh] Selected Intervention: CEA-Left | | | | | | Edit Assessment Intervention confirmed |

| Intervention | Clinical Summary | Guidelines | Risks | Assessment | Consent | Schedule |
|---|---|---|---|---|---|---|

Presentation

✓ Symptomatic Overridden
*Stenosis Overridden
  Low (< 50%)
  Medium (50-69%)
  High (70-89%)
*Very High (>=90%)

602

Required Questions

*Rapid Progression of Stenosis
  *yes
  no
*Enrolled in clinical trial
  yes
  *no
*Experienced non-disabling ischemic stroke

608

Procedural Risk

High risk co-morbid conditions
Unfavorable Anatomy for CEA
Unfavorable Anatomy for CAS

*Life Expectancy
  *>=5 yrs
  <5 yrs

604

Medical Therapy

☑ Antihypertensives 2013-07-24
☑ Antidiabetics 2013-07-03
☑ Statins 2013-07-05
☑ Anticoagulants 2013-07-24

606

600

< Back - Summary    Save    References    Explanations    Next - Risks >

FIG. 6a

Patel et al.
Appropriate Use Criteria for Diagnostic Catheterization

JACC Vol. 59, No. 22, 2012
May 29 2012:000-00

610 → Table 1.5. Patients With Known Obstructive CAD (e.g, Prior MI, Prior PCI, Prior CABG, or Obstructive Disease on Invasive Angiograhpy)

| Indication | | Appropriate Use Score (1-9) | |
|---|---|---|---|
| | | Asymptomatic / Controlled Symptoms OR Unchanged Findings | Worsening or Limiting Symptoms AND Worsening Findings |
| Medically Managed Patients (614) | | | |
| 49. | • Low-risk noninvasive findings | I (2) | U (6) |
| 50. | • Intermediate-risk noninvasive findings | U (4) | A (7) |
| 51. | • High-risk noninvasive findings | A (7) | A (9) |
| Post Revascularization (PCI or CABG) (616) | | | |
| 52. | • Asymptomatic or stable symptoms | I (1) | |
| 53. | • Low-risk noninvasive findings<br>• Worsening or limiting symptoms | | U (6) |
| 54. | • Intermediate-risk noninvasive findings<br>• Worsening or limiting symptoms | | A (7) |
| 55. | • High-risk noninvasive findings<br>• Worsening or limiting symptoms | | A (8) |
| Post Revascularization (PCI) (618) | | | |
| 56. | • Asymptomatic<br>• Prior unprotected left main PCI | | U (5) |

A=appropriate;CABG=coronary bypass grafting surgery;CAD=coronary artery disease;I=inappropriate;MI=myocardial infarction;PCI=Percutaneous coronary intervention;U=uncertain

FIG. 6b

☐ QPID PrOE                                                    Options  Legend  Feedback  Help
Test, Ignore (0000006) 40 /M    Visit Date: 2013-08-02  [Refresh]  Selected Intervention: CEA-Left   No edits yet.

Intervention  Clinical Summary  Guidelines  | Risks |  Assessment  Consent  Schedule

| CAS Risk of Stroke or Death | CEA Risk of Stroke or Death |
|---|---|
| *Major Non-vascular Surgery planned within 8 weeks<br>  ○ Yes<br>  ○ No<br><br>☑ Prior Stroke 2012-08-27<br>☑ AFib or Flutter 2007-01-04<br>☑ Prior Ipsilateral CEA 2005-12-05 | *Urgent Cardiac Surgery planned within 8 weeks<br>  ○ Yes<br>  ○ No<br><br>☐ Peripheral arterial disease<br>☐ Tracheostomy present<br>☐ Contralateral Occluded Carotid<br>☐ Severe Angina or low EF |

<Back – Guidelines        Save        References        Explanations        Next – Assessment>

☐ QPID ProE
Test, Ignore (0000006) 40 /M   Visit Date: 2013-08-02   Selected Intervention: CEA-Left   [Refresh]   Options Legend Feedback Help
Intervention   Clinical Summary   Guidelines   Risks   Assessment   Consent   [Schedule]   Edit Assessment   Intervention confirmed

ProE
PROCEDURE
DECISION SUPPORT

Patient:              TEST, IGNORE
MRN:                  0000006
DOB:                  1973-03-09
Procedure:            CAS
Details:              [Left]
Urgency:              ○ <2 weeks   ● 2-4 weeks   ○ 4-8 weeks   ○ >8 weeks
Performing Surgeon:   [Dr. Test]
Notes:

<Back – Consent                    Print                    Confirm Scheduled

☐ QPID Medicine    List: [None]    MRN: [9000006]    last 25   traditional QPID   feedback   about

TEST, IGNORE 40 /M
RC: N /A

[Search] ⓘ

Records [All ▾]
Notes
2012-11-29 NTE Patient Letter
2012-11-27 NTE Patient Note
2012-11-14 NTE RETURN
  1057 more
STUDIES [All ▾]
2009-03-18 CAR Cardiac Ultrasound-Stress
2009-03-17 CAR Cardiac Ultrasound-TEE
2002-05-15 CAR CARDIAC ULTRASOUND
RADIOLOGY [All ▾]
2012-04-25 RAD MRILumbSpnNe WO
2011-12-06 RAD MRIBrainWo
2010-09-17 RAD Outside-MRI Spine
  28 more
MICROBIOLOGY [All Cx ▾]
2004-06-15 MIC ED LAB SPECIMEN
  10 more
PATHOLOGY [All ▾]
No records found
Labs [Recent ▾]
No records found

Select Past Medical History — 1104

| CV | PULM | GI | GU | ID | Nuero | Heme | Other |
|---|---|---|---|---|---|---|---|
| AAA / Dexn | Asthma | Diverticulosis | AKI | | AMS | Anemia | Agitation |
| AFib / Flutter | COPD | | CKD | | Dementia | | Capacity |
| CAD | | GERD | Hematuria | | | HIT | Depression |
| Chest Pain | Hemoptysis | GI Bleeding | | | Headaches | Hypercoag | ELOH |
| CHF | | Hepatitis | | Fungal Infx | | | Drug Abuse |
| Conduction Dx | OSA | IBD | RRT | HIV / AIDS | | | Noncompliance |
| | PE | Intes.. Ischem. | Stones | | Seizures | Screening | Psych |
| Valve Disease | Pulm HTN | | UTI | TB | Stroke / TIA | TTP / HUS | Smoking |
| VT / VF | | | | UTI | | | |

Exam Findings

👍 This was useful   👍 This changed management   👍 This saved a test

| BP | Orthostatics | | | |
| CN Findings | Ulcer | | Echo | |
| EF | Weakness | | Endoscopies | Surgeries |
| Home 02 | Weight | | Hardware | |
| HR | | | | |
| MMSE | | | Pacemaker | |

Ops / Devices — 1108

— 1106

Common Workups — 1100

ARF
Ams
Anemia
Chest Pain — ARF
ECOH
Hypercoag
Rheum Workup
Sob

Syncope
Trasminitis — 1110

Last updated: Aug 9,2013 9:33:29PM    DATA UPDATED—CLICK HERE TO UPDATE AGAIN    1.0.0 Beta

1102

STRUCTURED SUPPORT OF CLINICAL HEALTHCARE PROFESSIONALS

CROSS-REFERENCE TO RELATED APPLICATIONS

This application represents the national stage entry of PCT International Application No. PCT/US2014/051652 filed Aug. 19, 2014, which claims priority to U.S. Provisional Patent Application Ser. No. 61/867,497, filed Aug. 19, 2013, both of which are hereby incorporated herein by reference for all purposes.

FIELD OF THE INVENTION

The present invention relates to systems and methods for facilitating clinically-relevant decisions and determinations and, more particularly, to a system and method for using information in the patient's medical record to determine appropriate treatments of a patient condition.

BACKGROUND OF THE INVENTION

Clinicians and physicians, including specialists such as radiologists, gastroenterologists, and particular types of surgeons, may need access to all of a patient's medical information in order to make the best diagnoses and treatment decisions. More commonly, the specialist needs access to certain aspects of a patient's medical history, but may not know in advance, or even during examination, which aspects will inform decisions. In particular, background information about the patient and the patient's medical history can aid the specialist in interpreting the results of any performed studies. However, the manner in which information is organized and stored in an electronic health record system may not correspond to the set of concepts that a clinician must evaluate in order to put in place an optimal treatment plan for the patient at hand. As a practical example, prior to initiating a particular surgery—for example, vascular surgery of the carotid artery to reduce the risk of stroke—the clinician should understand if the patient is already on maximal medical (non-surgical) therapy for this particular condition. The concept of 'maximal medical therapy for carotid artery vascular disease' may be well described in the literature and is typically described as part of the clinical guideline. However, this example concept of 'maximal medical therapy for carotid vascular disease' is far too granular and specific to be encoded in the database schema at the heart of an EHR system—even the most highly structured EHR systems are unable to encode the myriad clinical concepts that drive optimal decision-making. Further, the substrate information that would inform the clinician about this concept might be scattered in multiple places in the patient's record. Continuing the example, this information for the concept of 'maximal medical therapy for carotid artery vascular disease' might include a description of the classes medication specified for this condition. Further information to be extracted from the medical record of the patient includes references to medications given, medications not tolerated by patient, medications for which the patient has an allergy. This information might be scattered throughout unstructured clinic (text) notes, structured medication lists, or semi-structured problem lists. And when present, especially in unstructured information that comprises the majority of EHR information, the clinical concept may be only embodied in complex medical language reference, understandable to a human reader, but not encoded as a structured piece of information. Further, the patient's medical information is typically dispersed across multiple data stores, which may be electronic or non-electronic. As a result, the information-gathering burden for a clinician is frequently overwhelming because of a mismatch between the data schema of the EHR and the practical, clinical concepts that the specialist must evaluate in order to initiate a treatment plan. As a result, clinicians frequently make complex clinical decisions with limited information on hand. This dearth of relevant information in decision-making leads to inappropriate utilization of expensive healthcare resources and can, in some instances, even compromise patient safety.

Searches of a patient's electronic health record (EHR) can be extremely time consuming. For example, in a radiological (medical imaging) study, EHR searching can consume 20-53% of the total interpretation time of the study (ref: Lin et al, Am J Roentgenol 2010). Similar EHR searches may be performed in 27-64% of all Abdominal-Pelvic CT (ABP-CT), Transvaginal Pelvic Ultrasound (TV-US), and Brain MRI (B-MRI) studies. In a relatively large hospital, every week many hundreds of these studies may be performed. Therefore, a large amount of time and health care money is spent manually searching patient medical records for ancillary medical data.

Furthermore, treatment guidelines exist that are based on previous medical studies, such as clinical trials or procedure results, and these guidelines could help the specialist ascertain the appropriateness and risk of a particular procedure in light of a patient's characteristics. Of course, a specialist does not retain all medical knowledge in his or her own head, and the scope of medical literature on any particular subject could be unwieldy to efficiently search. As a result of their length and complexity, guidelines, typically informed from extensive clinical trial information, are generally impractical for the clinician to utilize in real time for patient care. The reason is that each is comprised of up to hundreds of clinical scenarios described by numerous clinical concepts, as in the preceding example (e.g., the concept of 'maximal medical therapy for carotid vascular disease'). In practice, the clinician is confronted by both an overwhelming complexity of decision guideline as well as an overwhelming information retrieval problem.

Therefore, it would be desirable to have a system and method for extracting clinical concepts required for a guideline from the medical record, making such information available to a given clinician, allowing him or her to evaluate these concepts and attest to their presence for a patient, and then reconciling the clinician's attestations against the description of best practice embodied in the clinical guideline.

SUMMARY OF THE INVENTION

The present invention relates to systems and methods for querying structured and unstructured data stores to present the patient's medical records and related information to guide clinical decisions using the patient medical information, draw inferences from the information, and ascertain whether treatment guidelines support one or more potential courses of treatment.

In some implementations, the present invention includes a method for generating a patient abstract containing data about a medical history of a patient. That data is selected from the patient's medical records for relevancy to one or more instructions. The method includes receiving the instructions, extracting at least one term from the instructions, and retrieving an ontology from at least one of an electronically-readable database and an electronically-readable memory. The ontology defines relationships between a plurality of terms, a plurality of medical concepts, and a plurality of data elements. The method includes using the ontology to identify at least one medical concept related to the at least one term extracted from the instructions, using the at least one medical concept and the ontology to identify at least one medical data element related to the at least one medical concept, accessing the medical records of a patient to retrieve data associated with the at least one medical data element, and accessing at least one external source to retrieve one or more guidelines for performing one or more interventions associated with the at least one medical data element. The method includes using a user interface to display at least a portion of the data associated with the at least one medical data element retrieved from the medical records. The method further includes using the user interface to display an assessment of one or more of the interventions.

In other implementations, the present invention includes a system for generating a patient abstract containing data about a patient selected from the patient's medical records. The system includes means for identifying at least one medical concept related to a provided term, and means for identifying at least one medical data element related to an identified medical concept. The system includes means for querying a database containing at least a portion of the patient's medical records for the identified at least one medical data element, means for querying at least one external source to retrieve one or more guidelines for performing one or more interventions associated with the at least one medical data element, and means for displaying at least a portion of a result from the queries.

In further implementations, the present invention includes a system for generating a patient abstract containing data about a patient selected from the patient's medical records. The system includes a plurality of computer systems, a database containing at least a portion of a medical record for the patient, and at least one external data source having information about at least one guideline for performing at least one intervention. The system also includes a communications network coupling the plurality of computer systems, the database, and the at least one external data source together to facilitate communication therebetween. The at least one computer system of the plurality of computer systems is configured to build a hierarchical tree using at least the at least one guideline, extract at least one term from a medical order for the patient, and identify at least one medical concept related to an extracted term. The at least one computer system of the plurality of computer systems is also configured to identify at least one medical data element related to an identified medical concept, query the database for the identified at least one medical data element in the medical record for the patient, and, using information from querying the database and the hierarchical tree, evaluate an appropriateness of the identified medical concept or the medical order for the patient under the at least one guideline. The at least one computer system of the plurality of computer systems is configured to generate a report at least indicating a result of evaluating the appropriateness of the identified medical concept or the medical order.

In still further implementations, the present invention includes a method for generating a patient abstract, the patient abstract containing data about a medical history of a patient, the data being selected from the patient's medical records. The method includes retrieving an ontology from at least one of an electronically-readable database and an electronically-readable memory, the ontology defining relationships between a plurality of terms, a plurality of medical concepts, and a plurality of data elements and using the ontology to identify at least one medical concept related to at least one term extracted from one or more entries in the patient's medical records. The method also includes using the at least one medical concept and the ontology to identify at least one medical data element related to the at least one medical concept and accessing the medical records of a patient to retrieve data associated with the at least one medical data element. The method further includes accessing at least one external source to retrieve one or more guidelines for performing one or more interventions associated with the at least one medical data element and generating a hierarchical decision tree from the one or more guidelines. The method also includes using a user interface to display at least a portion of the data associated with the at least one medical data element retrieved from the medical records and an interactive menu to guide a user through the hierarchical decision tree to arrive at an assessment of one or more of the interventions.

The foregoing and other aspects and advantages of the invention will appear from the following description. In the description, reference is made to the accompanying drawings which form a part hereof, and in which there is shown by way of illustration at least one embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 4, 5, and 7-11 are illustrations of user interface screens displaying a patient abstract.

FIG. 6a is a graphic illustration of a user interface for guiding clinician decisions relative to guidelines.

FIG. 6b is an example of a table reflecting an example of clinical guidelines.

DETAILED DESCRIPTION

Figure 1:
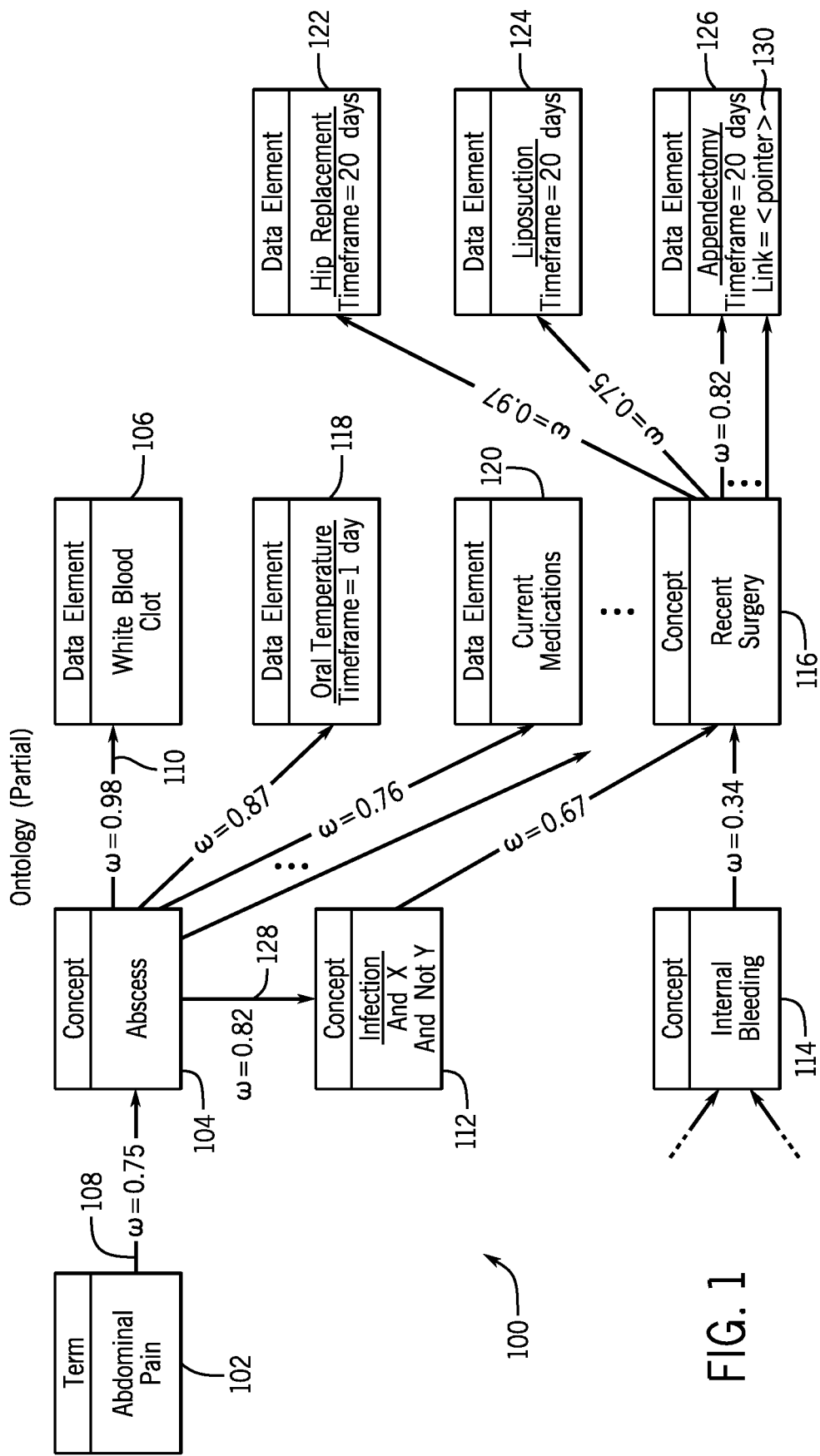
FIG. 1 is a block diagram of a data structure illustrating a portion of an example ontology for use in conjunction with systems of the present invention.

Though electronic medical records and various computer and other management system for electronic medical records have become a key component of modern and evolving healthcare institutions and practices, much of the promise of electronic medical records has not been realized because of the lack of systems to manage the substantial and diverse information stored in such records in a way that facilitates healthcare outcomes. As will be described, the present disclosure provides a variety of systems and methods that facilitate clinician decisions and, in particular, decisions relative to treatment guidelines. For example, as will be described, the present disclosure provides systems and methods for providing clinicians with relevant patient information to expedite the clinician's review of the patient's history and/or requests specific information. Furthermore, the present disclosure provides systems and methods that facilitate the creation of robust data structures—conceptual queries—without placing an undue burden on the record keepers. For example, as will be described, the present disclosure leverages ontology to create robust and complex data structures and deliver clinically-relevant information to facilitate healthcare outcomes relative to treatment guidelines.

As will become apparent from the description provided below, methods and systems are disclosed for automatically generating a patient decision abstract (also referred to herein as a "patient abstract", "abstract", or "queried patient abstract") that contains all or selected portions of a patient's medical history, and may further contain other medical information that is not specific to the patient but may be related to the patient in terms of assessing the propriety of certain treatments or other actions. In one implementation, the information presented in the patient decision abstract is anticipated to be of relevance to a specialist who will analyze a patient's study, perform a procedure or otherwise treat or diagnose the patient.

The method and apparatus can have utility in many different settings to aid in identifying any number of symptoms or possible medical conditions of a patient, or requests that particular tests or examinations of a patient be performed. For example, in one setting, the abstract may be generated upon registration of the patient at a treatment facility, such as in the emergency department patient tracking system of a hospital, prior to any physician or nurse attending to the patient. The patient abstract allows for review of pertinent elements of the patient's history that might prove critical for optimal care delivery in the emergency department. In another setting, a physician at a laboratory, treatment facility, or the like receives a medical order (or more simply an "order") for studies or procedures to be performed on a patient. From information contained in the order, inferences are automatically drawn about the purpose for the order, including the nature of the patient's situation or condition. These inferences are then used to identify data items that may be present in the patient's medical records and that, if present, are likely to be of interest to the specialist. The patient's medical records are queried for the identified data items, and retrieved data items are displayed to the specialist in a patient abstract. The retrieved data items in the patient abstract may be displayed as excerpts from the patient's medical record.

The patient abstract can be generated before the specialist begins examining the patient or performing and evaluating patient studies, providing treatment, or performing a requested procedure. Using the patient abstract, the specialist can save time that would otherwise be occupied by deciding what background information to obtain about the patient and by querying numerous databases to retrieve the information from the patient's medical records. Additionally, because data may be selected for inclusion in the patient abstract based upon information contained within a medical order or other instruction, the abstract is likely to provide the specialist with highly relevant data in a compact form, thereby optimizing the specialist's reading time.

Additionally, because the system is rule based and obtains data, rules, or guidelines from medical information sources that are not particular to the patient, the patient abstract includes data items that the specialist may not otherwise have requested, such as due to fatigue, lack of experience or error, or obscurity of the relationship between the reason for the examination and the data item. Thus, the system may provide two additional benefits over existing electronic health systems: 1) an ability to guide the clinician end-user through an accepted canon of conceptual questions driven by the clinical guidelines relevant for that particular clinical scenario—e.g., contemplated carotid vascular surgery) and 2) the ability to alert the specialist to useful background data—information that the specialist could not otherwise review due to the difficulty of retrieval and the organization of information. (e.g., the system can make the specialist aware of the complete list of medications relevant for carotid vascular disease that the patient has already received). Furthermore, as more is learned about relationships among diseases, causes and ascertainable facts or diagnostic values, the rules may be augmented or updated to the benefit of users of the system.

The patient abstract may be displayed in a user interface that arranges the information in the patient abstract according to treatment goals. For example, the patient abstract may be divided into sections that separately set forth possible interventions (i.e. procedures, therapies, laboratory tests, and the like), a clinical summary of the patient's medical history, guidelines for selected interventions, an assessment of risks of each proposed intervention. The user interface may provide a zero-click presentation of query results that provides detailed information about displayed excerpts from the medical record, as described below. The user interface may further include sections that provide interactive tools to the specialist for obtaining patient consent for selected interventions, and for scheduling procedures and the like.

In the present system, a patient abstract may be generated based upon a medical order or other input containing information about a patient. The input is analyzed to generate inferences about the purpose of the medical order using rules identifying data that may be relevant to that purpose. The inferences may be drawn from a particular question presented in the medical order, or other text or information in the order.

Because a medical order may include a variety of words, phrases, or other information (collectively "terms") that refer to similar concepts, the present system may use a concept map to connect each term in the order to one or more concepts. Each concept can then be expanded to include related concepts or data points that can then be searched for in the client's medical history. For example, the term "abdominal pain" may appear in a medical order. The medical order is processed, and the term "abdominal pain" can then be mapped to the various concepts including "abscess," "indigestion" and "appendicitis." Each identified concept can then be used to identify one or more data elements that may appear in a medical record. The patient's medical records can then be queried using the identified data elements, and results of the query are presented as a resulting patient abstract. The specialist may explore the patient abstract and perform further queries on desired concepts, terms, excerpts, or other information in the abstract by simply hovering an input pointer over the desired word or phrase, resulting in a pop-up display having detailed information about the word or phrase. Further pop-up displays may be associated with words or phrases in the first pop-up display, creating a tunneling information discovery interface that does not require the specialist to click on any terms.

Ontology-Based Term/Concept/Data Element Mapping

To provide for the mapping of terms found in medical information from relevant data stores to a set of concepts, the present system may use an ontology. As described herein, the ontology is a data model that represents a domain (in the present disclosure, the domain may include diagnostic or therapeutic medical information). Within a particular domain, the ontology identifies objects (e.g., terms, concepts, or data) that reside within that domain and specifies relationships between those objects. By categorizing the information presented by the ontology into three categories—terms, concepts, or data—the ontology can be simplified compared to other mapping structures that would map terms directly to data elements. By including the intermediary object of a 'concept' between terms and data elements, the mapping can be simplified as each term and data element will only be related a comparatively small number of intermediary concepts. If the ontology only mapped terms to data elements, each term would be mapped to many data elements, and each data element would be mapping to each term resulting in possibly millions of interconnections. As such, the inclusion of the 'concepts' into the ontology described below acts to compress or otherwise simplify the ontology, facilitating management and implementation of the ontology. For example, if a new term is introduced into the ontology, that term may only need to be connected to a small number of concepts, that, in-turn, connect to many data elements. Accordingly, the addition or removal of terms or data elements when using the ontology configuration described below is greatly facilitated.

FIG. 1 is an illustration of a portion of an exemplary ontology 100 that can be used in one implementation of the present system. Within FIG. 1, each block represents a term, concept, or data element (collectively "objects"). Block 102, for example, represents the term "abdominal pain," while block 104 represents the concept "abscess", and block 106 represents the data element "white blood count." Each term within the ontology may be directly related to one or more data elements or concepts, as indicated by arrows in FIG. 1 connecting term blocks to concept blocks, and each concept may be directly related to one or more other concepts and/or data element identifiers. For example, in ontology 100, the term "abdominal pain" 102 is directly related to the concept "abscess" 104, as indicated by arrow 108, and the concept "abscess" 104 is directly related to the data element identifier "white blood count" 106, as indicated by arrow 110.

Similarly, several objects within ontology 100 may be directly related to a single object. For example, both the concept "infection" 112 and the concept "internal bleeding" 114 are directly related to the concept "recent surgery" 116. Two objects are "indirectly related" if they are related to each other through at least one other object. For example, "abdominal pain" 102 is indirectly related to "infection" 112 and to "recent surgery" 116.

Starting with a term, such as "abdominal pain" 102, a set of directly and indirectly related concepts, such as "abscess" 104, "infection" 112 and "recent surgery" 116, can be identified using ontology 100. The identified concepts are said to be inferred from the term or from the medical order. Using concepts that are indirectly related to terms found in a medical order enlarges the scope of concepts found, and therefore the possible list of data items displayed, by the system.

A patient's medical records may contain a wide variety of laboratory data, reports, x-ray images, physician notes, and the like. Some of this information may be structured numerical data. For example, a complete blood count (CBC) usually includes white blood cell count, white blood cell types, red blood cell count, hematocrit, and the like. Other information in the medical records may be in the form of unstructured expository text, such as physician notes, family history records, and the like.

A patient's medical records may be stored in a single database; however, more frequently, the medical records of a single patient are distributed across several databases. These databases may be physically located in disparate locations. Each of the locations may be associated with one or more of a plurality of different organizations, such as independent laboratories, hospitals, clinics and doctor offices, where the patient has been seen. A single organization may maintain more than one of these databases. For example, a hospital's radiology department may maintain a database of imaging studies (such as x-ray, ultrasound and computed tomography (CT) images and written analyses generated therefrom), and the hospital's blood laboratory may maintain a separate database containing blood studies.

Ontology 100 also includes blocks that represent data elements that may be found in a patient's medical records. For example, block 106 represents the data element "white blood count," block 118 represents the data element "oral temperature," block 120 represents a list of "current medications," block 122 represents "hip replacement" surgery 122, block 124 represents "liposuction" surgery, and block 126 represents "appendectomy." Each data element defines one or more of text strings, database columns, or other mechanisms allowing data corresponding to each data element to be retrieved from the patient's medical record.

A patient's medical records may, of course, contain multiple instances of a given data element. For example, the medical records may contain several white blood counts, each taken on a different day. However, the contents of ontology 100 are not related to the number of instances of a particular data element in a patient's medical records. Ontology 100 is used to identify one or more distinct data elements (such as "white blood count" or "liposuction") that are related to a given term (such as "abdominal pain"). Another portion of the system then queries the medical records databases to locate instances of the identified data element with the patient's medical record, if the databases contain any such instances.

Each concept in ontology 100 is mapped to one or more data elements that may be of relevance to a specialist conducting a study that relates to the concept. For example, if a specialist is conducting a study related to abdominal pain 102, the specialist may be concerned that the pain is caused by an abscess 128 or by an infection 112. With respect to the possibility of an abscess, the specialist is likely to find the patient's white blood count 106, oral temperature 118 and current medications 120 relevant to any analysis, because this information may make one diagnosis more likely than another. Similarly, with respect to the possibility of an infection 112 caused by a recent surgery 116, the specialist is likely to find it relevant if the patient has undergone a hip replacement 122, liposuction 124 or appendectomy 126.

Optionally, timeframes and/or other selection criteria or selection logic may be associated with a particular object within ontology 100. For example, each of the surgery data elements 122-126 shown in ontology 100 includes a defined timeframe. Only surgeries that occurred within that timeframe prior to the time at which the patient abstract is generated will qualify for inclusion in the patient abstract.

As such, the selection criteria can be used to prevent stale or old information from being included in the patient abstract.

Other non-limiting examples of possible selection criteria include minimum or maximum data values and words, phrases or other text strings that must (or must not) appear in the data value in order to qualify the data element for inclusion in the patient abstract. For example, an oral temperature greater than 100 degrees Fahrenheit or below 97 degrees Fahrenheit may indicate an infection or other problem. Accordingly, a temperature data element may have selection criteria associated with it that limits inclusion of temperature data elements in the patient abstract unless the temperature falls outside of 'normal' levels. Similarly, blood work results may include selection criteria so that normal blood work reports are not included in the abstract. For example, selection criteria may specify that blood work data should only be included in the patient abstract if the blood work indicated the presence of white blood cell types at sufficient levels to indicate an allergic or toxic reaction to medicines or chemicals or indicate a condition, such as leukemia.

Each data element may also be associated with alert criteria. The alert criteria may describe certain ranges of values that, if a particular data element satisfies those values, the data element may be of critical importance to the specialist. For example, body temperature measurements that are exceedingly high may warrant alert status. Alert criteria may further be assigned varying degrees of importance. For example, a body temperature may be abnormal but not exceedingly high, and such a temperature may warrant an alert status that the temperature is abnormal, in contrast to it being exceedingly or critically high.

Each object within ontology 100 may also include Boolean selection criteria that must be satisfied before the data element is included within an abstract. For example, the concept "infection" 112 includes two Boolean selection criteria: "AND x" and "AND NOT y." For the concept "infection" 112 to be included, condition "x" must be TRUE and condition "y" must be FALSE. A condition may refer to another object. For example, the "infection" concept 112 may require another concept (such as "entry point") to have been inferred as a result of some term in the order or some other concept having been inferred.

Each data element in ontology 100 can also be assigned an "always search" status. In that case, regardless of the terms included in the medical order, those data elements are always search for in the patient's medical records. For example, data elements such as blood pressure, weight, age, or procedures having occurred in the last week, could always be included in a patient's abstract. The always include requirement could be assigned to either concepts or data elements as shown in ontology 100.

Optionally, each relationship in ontology 100 may be assigned a weight. For example, in ontology 100 represented in FIG. 1, the relationship 108 between "abdominal pain" 102 and "abscess" 104 has a weight w=0.75. Weights may be allocated according to an arbitrary scale, such as floating-point numbers between zero and one (0.00 to 1.00), or any other suitable continuous or discrete scale. A relationship's weight may represent a strength of the relationship between the two related objects, i.e. the weight may quantify a level of certainty that the inclusion of the first object (term) in a medical order (or the inference of the first object from a medical order) indicates that the second object should be inferred from the medical order.

In one implementation, only relationships having weights that exceed a threshold value are used to draw inferences. In that case, to draw inferences using objects in a chain of relationships, such as the chain between the term "abdominal pain" 102 and concept "infection" 112 in ontology 100, the average of the weights between pairs of the objects in the chain must exceed a threshold value. The threshold value(s) may be predetermined or dynamically set, such as based upon a sensitivity parameter that is set by a user or system administrator. In other implementations, the weight values are multiplied together to identify objects selected from the ontology that are to be used in generating the patient abstract. For example, when moving along a chain of related concepts, the system first verifies that the weight of the relationship between the first two objects exceeds a particular threshold. If so, the system then multiplies the first two weights along the chain between the first three objects together and determines whether the multiplied value exceeds the threshold. If so, then the first three objects are valid and will be used in generating the abstract. Then, the system moves on to multiply the first three weights between the first four objects in the chain together and determines whether the result exceeds the threshold. This process repeats until the multiplied value of the weights no longer exceeds the threshold. At that point, the system only includes objects selected from the portion of the chain for which the multiplied weights exceeded the threshold, ignores the remaining objects and moves on to the next chain.

The weights may also be adjusted based upon a status of the medical order. If the order is an emergency order, the weights could be adjusted to generate a patient abstract that is much more focused on the particular issues that are being faced by the specialist. Older information, or information that is only slightly related to the questions at hand could be excluded from the abstract to allow the specialist to quickly focus on the most relevant information possible. Alternatively, if the order indicates the presence of idiopathic symptoms, for example, the weights can be adjusted to include more information in a particular abstract. That way additional information that may otherwise have been excluded can be presented to the specialist, but which may ultimately be relevant to making a determination as the source or cause of the symptoms.

In one implementation, a single ontology can be developed for use in generating patient abstracts for a number of different specializations. Because different objects within the ontology may have different levels of relevance to different specialties, though, different weighting systems can be developed for the different specialties. For objects that are of lesser relevance to a particular specialty, the weights for those objects can be reduced, while the weights for objects that are relevant can be increased. As described below, the present system allows for a specialist reviewing a particular patient abstract to provide feedback on the usefulness of the information presented in the abstract. The feedback can then be used to modify and adjust the weighting system for that specialty accordingly.

In another implementation, given a particular set of input terms, certain data elements may be indicated being mandatory before a particular abstract can be generated. If, for example, a particular written order asks a specialist to analyze some blood test results, the system will only generate a patient abstract for the specialist if the results of that blood test can be found in the patient's medical history. If the results cannot be found—perhaps because the test has not be run yet—the processing of the patient abstract will be put into a hold state until the test results are available. This avoids wasted time that a specialist would otherwise take to find test results that haven't been generated yet.

Optionally, one or more of the objects may each include one or more links, exemplified by a link 130, indicating that related information is available. The related information may be, without limitation: one or more other objects within the ontology; one or more data elements retrieved by the system from one or more data stores; one or more pointers, such as a hyperlink, to sources of related information stored in locations other than the patient's medical records; or other related information. The related information may include explanations of the relevance of concepts or data elements to terms or concepts; medical texts, treatises, articles or the like or portions thereof that provide background information on various concepts; contact information (e.g., links to web pages, email addresses, or other contact information) for laboratories, service providers or people who may be consulted in relation to a particular subspecialty; policies and procedures related to diagnosis or treatment of related conditions; information about related medical procedures; reporting requirements for related diseases, such as HIV and AIDS; or the like. Some or all of the sources may be co-located with the ontology; however, some or all of the sources may be located within, and managed by, other organizations or entities. Exemplary sources include the National Library of Medicine maintained by the National Institutes of Health and the Public Health Image Library maintained by the Centers for Disease Control and Prevention.

Patient Abstract Generator

Figure 2:
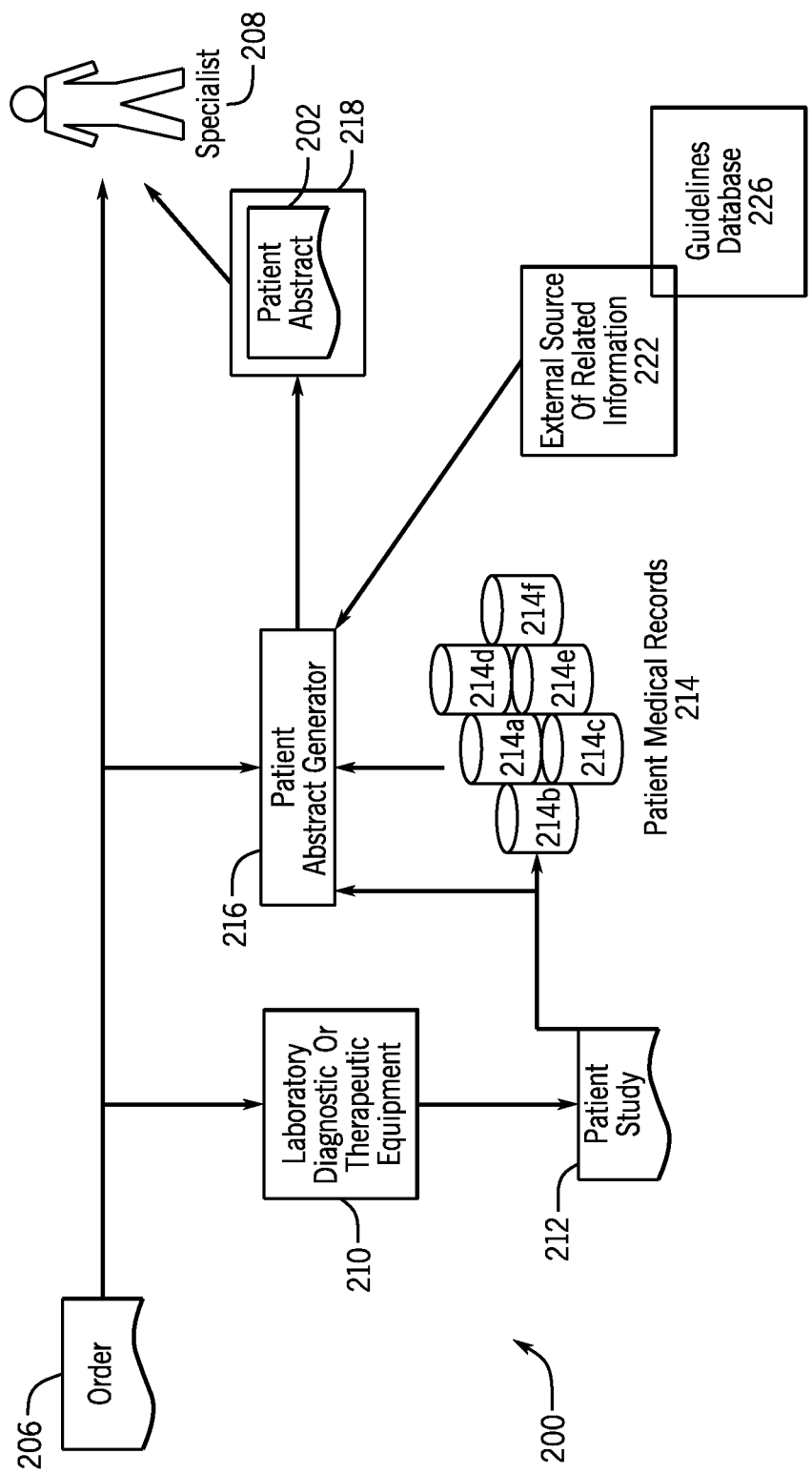
FIG. 2 is a block diagram showing functional components of a computerized system in accordance with the present invention.

Referring now to FIG. 2, an exemplary embodiment of a computerized system 200 for generating a patient abstract 202 is shown. The patient abstract 202 is generated by a patient abstract generator 216, which performs queries of one or more data stores to obtain the medical information for the patient abstract 202, processes the medical information according to one or more rule sets as described below, and formats the processed medical information for display to a specialist 208 as the patient abstract 202 in a user interface.

The data stores may include equipment that generates report data, such as laboratory, diagnostic, and/or therapeutic equipment 210. Laboratory, diagnostic and/or therapeutic equipment 210 is typically involved in executing procedures and performing studies 212. In the example of a suspected infection, the equipment 210 may include blood analysis equipment designed to culture a blood sample and detect one or more strains of infectious bacteria. Equipment 210 may also be used to deliver a treatment to the patient. For example, equipment 210 may include kidney dialysis equipment. The equipment 210 may process instructions, such as commands manually entered by the specialist or staff or instructions from an order, and may produce data that may be delivered to the patient abstract generator 216 and/or stored in patient medical records databases 214 as described below.

A laboratory test, such as an x-ray or a blood test, typically results in a study 212 that contains raw results of the test. The study 212 is typically delivered to the specialist 208 for analysis. As noted, the study 212 (either in its entirety or as individual data items), as well as previously performed studies, physician notes and other data about the patient, may be stored in one or more additional data stores accessible by patient abstract generator 216, exemplified by medical record databases 214*a*, 214*b*, 214*c*, 214*d*, 214*e* and 214*f*, generally denoted 214. Other numbers of databases can, of course, be used. Collectively, medical record databases 214 contain the patient's medical records. A study 212 may additionally or alternatively be directly delivered to or queried by the patient abstract generator 216.

Medical record databases 214 may be of various types and sizes. Each of the medical record databases 214 need not be in identical or compatible formats. Some data may be duplicated in more than one of medical record databases 214. Some data may be stored "off line," such as on removable computer media, such as optical discs or magnetic tapes. Thus, accessing some of the data, or some patients' data, may take considerably more time than accessing other of the data or other patients' data. It should be noted that generating some or all of patient abstract 202 before specialist 208 takes up study 212 saves specialist 208 time, because specialist 208 need not formulate a query nor wait for medical record databases 214 to respond.

Data stores may further include external sources 222 of related medical information stored in a location other than the medical records (i.e. databases 214). External sources 222 may contain data in structured or unstructured formats. Some structured formats, such as the service-oriented-architecture ("SOA"), have a self-described schema that presents to the consumer of the service (which may manage queries to the external source 222) an explanation of the particular data elements returned by the service. The system may be configured to thereby "learn" the data structures of such external sources 222 and retrieve relevant data. In other embodiments, one or more known data schema may be hard-coded into the system, such as through installation of one or more data query libraries such as SQL, XML, or other media types. In the absence of a known data schema, the system may index and search all the data returned for the particular language elements described in the saved conceptual searches. In this approach, the natural language processing built into each saved conceptual query permits the extraction of information from the medical record data store even if a structured data schema is not provided.

External sources 222 may include one or more guideline databases 226. Guideline database 226 may include data available from clinical trials or registries that pertains to the usefulness or efficacy of certain treatments in certain subpopulations. Such data in a guideline database 226 may be aggregated for the purpose of developing classifications of recommendations for one or more treatments. A guideline database 226 may include such classifications, retrievable by the patient abstract generator 216, or the patient abstract generator 216 may retrieve the raw data and compile the classifications using its own processes described below. External sources 222 may contain resources, such as documents, websites, and the like, that are referenced by objects in the ontology, such as with links 130. For example, if a term, concept or data element object that at least in part caused a particular data item to be included in the abstract 202 includes a hyperlink to an external source 222 of related information, the specialist 208 may invoke the hyperlink, and the related information is fetched and displayed on the computer screen 218, as described further below.

Figure 3:
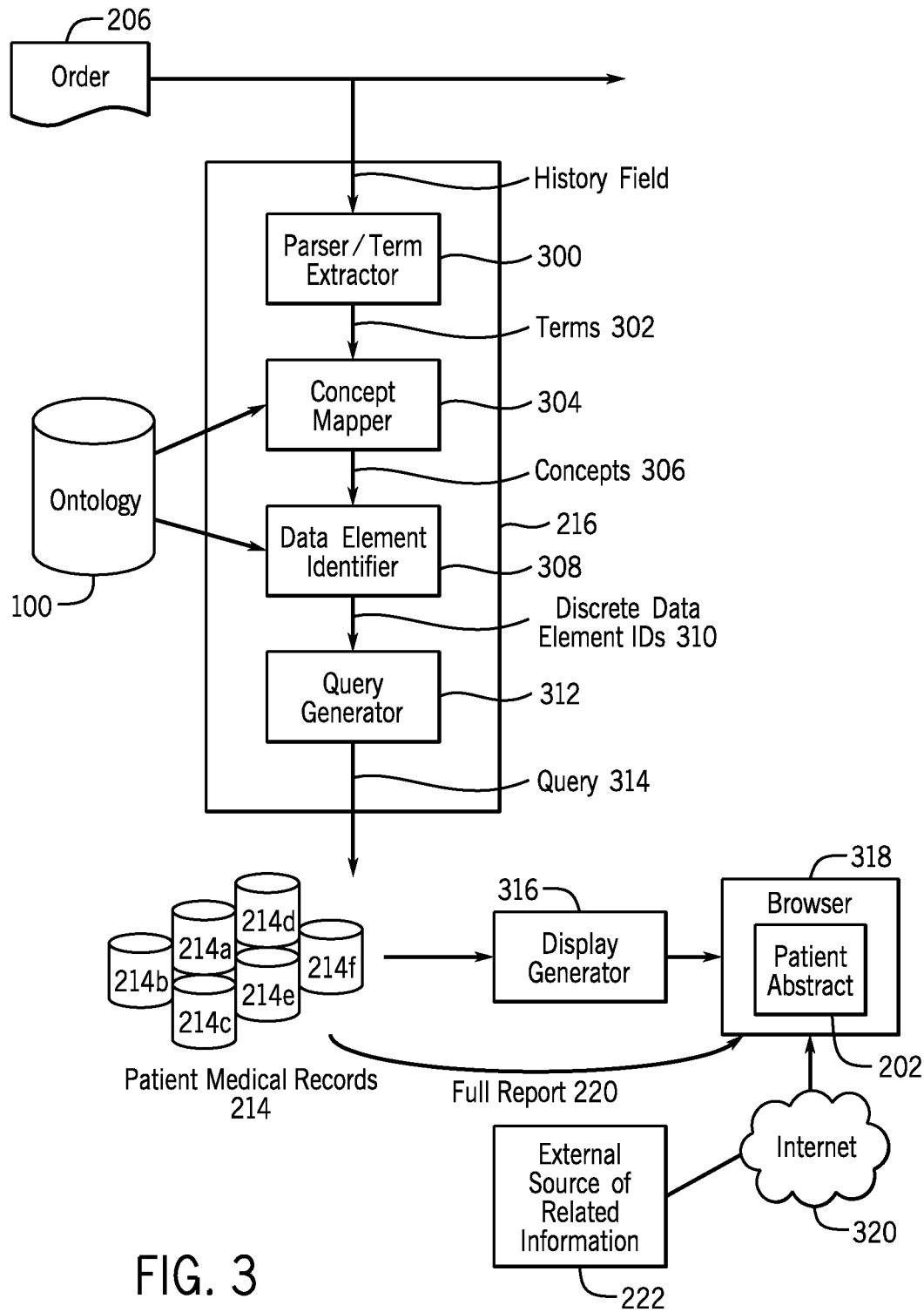
FIG. 3 is a block diagram showing components of a patient abstract generator as shown in FIG. 2.

Referring now to FIG. 3, the exemplary patient abstract generator 216 of FIG. 2 includes a number of components that progressively derive and generate one or more queries of the data stores. The queries may be derived from instructions provided to the patient abstract generator 216. The instructions may be a written or electronic order 206, a patient registration record, an information request directly entered by the specialist 208, or another type of data entry that indicates a patient abstract should be generated. Alternatively, the queries may be undirected and may return substantially all information relevant to the patient's medical history. FIG. 3 illustrates the processing by the patient abstract generator 216 of an order 206, but it will be understood that the described processing may be performed on any type of instruction.

The first component of the abstract generator 216, a parser/term extractor 300, reads all or a portion of the order 206 to extract terms (sometimes referred to herein as the "extracted terms"). In some implementations, the extractor 200 reads a history field or other field in the order 206 that includes the question presented by a referring clinician. When order 206 is handwritten, parser/term extractor 300 may include a scanner and optical character recognition (OCR) system for scanning an image of order 206 and converting the image of order 206 into a machine-readable text format. In one implementation, the scanner first scans a digital image of order 206 into an electronically-readable memory. The OCR system then accesses the electronically-readable memory and converts at least a portion of the digital image of order 206 into machine-readable text by converting the imaged letters of order 206 into their corresponding ASCII codes, or any other machine-readable code for representing the content of order 206.

The fields of the order 206 are typically not written according to a rigorous vocabulary or protocol. In addition, some or all of the fields in the order 206 may have been entered by a secretary or other non-medical person transcribing information dictated by the referring clinician 204. Thus, terms may be misspelled, abbreviated or inconsistently used. Furthermore, more than one term may be used in a single order 206 or across several orders to refer to a single concept.

The extractor 300 parses the field(s) input from the order 206 to ignore "noise" words, such as "and" and "or," to extract likely relevant terms. The extractor 300 may include a predefined list of key terms to be extracted, if any of the terms are found in the order 206. Optionally, the list of key terms may include common misspellings of terms and/or the extractor 300 may include an automatic spelling corrector. Optionally or alternatively, the extractor 300 may include a predefined list of noise words, which are not to be extracted. The extractor 300 may include further natural language processing abilities. For example, the extractor 300 may be directed to extract only semantically positive detections of a word, concept, word fragment or phrase (e.g., "patient has congestive heart failure" as opposed to the negative reference—"patient has no evidence of congestive heart failure"—or family reference, "patient's mother has congestive heart failure"—or conditional reference, "patient might have congestive heart failure"). In another example, the extractor 300 may be configured to process word fragments, such as the suffix "-carcinoma" (latter indicating presence of malignancy). In this way, the user can leverage the syntax, structure, and etymology of medical language in the specification of conceptual references found in the electronic medical record. Extracted terms 302 are passed to the next component of the abstract generator 216.

Concept mapper 304 infers concepts 306 from the extracted terms 302, as discussed above, using an ontology such as that illustrated in FIG. 1. Inferring concepts 306 from the extracted terms 302 is also referred to as "mapping" the extracted terms 302 to the concepts 306. In some implementations, the concept mapper uses an ontology 100 (see, for example, FIG. 1); however, in other embodiments, the concept mapper 304 may use a relational, flat or other type of database, in-memory data structures similar to the blocks shown in FIG. 1 or any other suitable data store or data structures to store information about term-to-concept relationships.

When using an ontology, the system first identifies terms within the ontology that match terms retrieved from the medical order. Then, those matched terms are used to navigate the ontology to identify related concepts. As discussed above, the identification of concepts associated with particular terms may involve verifying that the weight of the relationship between the term and the identified concept exceeds a particular threshold. When numerous terms or concepts are related though a chain, this process may involve combining the associated weight of objects in the chain (e.g., via averaging, multiplication, or other methods) to verify that the weighting of the related terms and concepts is sufficiently high.

Data element identifier 308 identifies data elements 310 from the inferred concepts 306, as discussed above, with respect to FIG. 1. Identifying data elements 310 from the concepts 306 is also referred to as mapping the concepts 306 to the data elements 310. In some implementations, the data element identifier 308 uses an ontology such as ontology 100 shown in FIG. 1; however, in other embodiments, the data element identifier 308 may use a relational, flat or other type of database, in-memory data structures similar to the blocks shown in FIG. 1 or any other suitable data store or data structures to store information about concept-to-data element relationships.

When using an ontology, the system first identifies data elements that are related to the concepts identified in the preceding steps. As discussed above, the identification of data elements associated with particular concepts may involve verifying that the weight of the relationship between the concept and the identified data element exceeds a particular threshold. When numerous concepts or data elements are related though a chain, this process may involve combining the associated weight of objects in the chain (e.g., via averaging, multiplication, or other methods) to verify that the weighting of the related concepts and data elements is sufficiently high.

Query generator 312 generates one or more queries 314 to one or more of the databases 214, based upon the identified data elements 310. Each query is formulated according to syntax, access credential, communication or any other requirements of the respective database 214a-f that is queried. For example, if one of the databases 214 is a relational database (RDB), a structured query language (SQL) query may be generated. The queries may conform to the Health level 7 (HL7) protocol. If one or more of the databases 214 includes security features, such as features to make the database compliant with the Health Insurance Portability and Accountability Act (HIPAA), the query may include a username, password and/or other appropriate credentials or safeguards. If one or more of the databases 214 is remote from the abstract generator 216, the query may be sent via the Internet or another appropriate local or wide-area, public or private network, such as the Internet, a virtual private network link or other suitable network connection. Similarly, the query generator 312 may generate one or more queries 314 for data stores other than the medical records databases 214, such as for one or more guideline databases 226 or other external sources 222.

Display generator 316 receives results of the query or queries 314 and generates displayable data. This data may be displayed by a purpose-build computer application or by a general-purpose application, such as a browser 318. If the data is to be displayed in a browser 318, the data may be formatted according to a markup language, such as the Hypertext Markup language (HTML). The display may include the patient abstract 202 formatted for navigation and/or interaction by the specialist 208 through a user interface, such as the user interface described below. Additional portions, or all of, the medical records 214 may be displayed by the display application or made accessible via the display. The display application, such as the browser 318, may retrieve the additional information from any of the described data stores 214 for display. Objects in the ontology 100 or another mechanism used to store term, concept, or data element relational information may include hyperlinks to resources stored in the external sources 222. The display generator 316 may include such hyperlinks in the displayable data in relation to data elements that were selected for inclusion in the patient abstract 202. A display application, such as the browser 318, may fetch the resources identified by the hyperlinks, such as via the Internet 320.

System Interaction and Clinician Guidance

FIGS. 4-11 illustrate exemplary communications in which the patient abstract 202 is presented to the specialist. The exemplary communication interface demonstrates illustrates one way of organizing the information retrieved by the system and presenting it for review and interaction by specialist or clinician. Other approaches may be implemented without deviation from the disclosed system and methods. To facilitate a specialist's work flow, the user interface may include section navigation 402, such as a series of tabs that each link to a section of the patient abstract 202. For each patient, the display may include patient information, such as a patient name 404, patient identification number 406, and status information 408 regarding details of the patient's visit, such as visit date, intervention(s) for which guideline, risk, and assessment information will be displayed as described below, and whether a selected intervention has been confirmed by obtaining consent and scheduling the intervention as described below.

Referring to FIG. 4, an intervention screen 410 may display information regarding one or more potential interventions that may be performed and require evaluation using the information in the patient abstract. The selection of interventions to display may be made manually by the specialist, according to which procedures the specialist wishes to have supported. Alternatively or additionally, the selection of interventions may be made automatically according to terms extracted from the instructions and/or the clinical grouping of similar alternative procedures. In the latter case, the groupings may be based on domain expert interview and medical literature review to determine which procedures are clinically related alternatives (e.g., carotid endarterectomy versus carotid artery stenting, versus medical therapy).

Referring to FIG. 5, a clinical summary screen 500 may display select aspects of the patient's medical history, as obtained through querying of medical record databases 214. In some embodiments, the clinical summary may be organized according to a category structure that aligns with the concepts or objects of the ontology. For example, as illustrated, the clinical summary screen 500 is divided into: selected labs 502, which lists all or a subset of laboratory studies 212 and may include the type of lab, the result, and the date on which the lab was performed, wherein the displayed lab may be one of several of that type, and may be the most relevant lab or the most recent lab; recent reports 504, which lists report types that specialists commonly should review, such as past medical history, advance directives, lists of past or current medications, and the like; notes 506, which may include notes previously made to the patient's medical record by other physicians; selected searches 508, which lists concepts, terms, or data elements from the ontology that the patient abstract generator 216 considers relevant to the potential interventions, and has used as keywords to query the medical record databases 214; diagnostic studies 510, which lists the diagnostic studies that the patient abstract generator 216 has determined from the ontology may be relevant to the potential diagnoses and/or potential interventions for the patient; and selected problems 512, which lists potential diagnoses based on the results of queries to the medical record databases 214 and their ontological relationships to the diagnoses.

The user interface may be configured to display detailed information about each of the listed terms, categories, or data elements upon request from the specialist. In one embodiment, the specialist makes the request by moving an input cursor, such as a mouse pointer, over the result. This instructs the user interface to produce a popup 514 containing the detailed information, which may include query results. For example, popup 514 is produced when the specialist "mouses over" the term "PFO" ("patent foramen ovale") in the selected searches 508. The popup 514 contains the single result from a query to the medical records databases 214 for the term PFO or phrase "patent foramen ovale," which is a discharge summary from a patient visit on Jan. 9, 2010. In one embodiment, the patient abstract generator 216 performs the query that returns the information in the popup 514 before the specialist requests it. In another embodiment, the patient abstract generator 216 performs this query at the time the specialist requests it, producing real-time, and therefore current, results.

The user interface may be further configured to produce "nested" detailed information by linking further queries to terms in the information displayed in the popup 514. This allows the user interface to display abbreviated versions of query results that contain a large amount of information. For example, popup 514 displays about two lines worth of text from the relevant discharge summary. The specialist may mouse over this text, which will display a second popup containing the full text of the discharge summary, or a larger relevant portion thereof. The specialist can also mouse over the result category "DIS" (for "discharge") to display a popup of all or a subset of the patient medical record data elements classified in the DIS category. The specialist can also mouse over the date to display a popup of all or a subset of data elements entered with that date. Each popup may include text that links to further popups, allowing the specialist to "drill down" on a particularly relevant topic without having to click on hyperlinks or perform other input.

If a medical order 206 or other instruction was provided to inform the patient abstract generator 216 which objects and data elements would carry the most weight, the select aspects listed on the clinical summary screen 500 may include the data elements of the patient's medical records that the patient abstract generator 216 determines are relevant to the instruction. For example, upon parsing the order 206 as described above, the patient abstract generator 216 may determine from the ontology that particular sets of labs, reports, notes, diagnostic studies, potential diagnoses, and record search terms are relevant to the order 206. The patient abstract generator 216 may perform the relevant queries and then format the results into the displayable abstract 202. In some embodiments, the clinical summary screen 500 may display only the categories, terms, or data elements if the related queries produced results from the medical records databases 214. In other embodiments, the clinical summary screen 500 may include all of the categories, terms, or data elements queried, even if no results were obtained. This demonstrates to the specialist that the patient's medical history was searched and contains no entries pertaining to that subject.

The user interface may emphasize or de-emphasize text according to the query results and their relevance to the instruction or selected intervention. In one embodiment, if a query result was obtained but its characteristics are within an established normal range, the entry on the clinical summary screen 500 may appear in a normal font (see "PLT" in the selected labs 502 and "Past Med History" in the recent reports 504). In contrast, where the result is abnormal or otherwise requires attention, the entry may appear in bold or otherwise emphasized letters (see "PT-INR" in the selected labs 502, "Advance Directives" in the recent reports 504, and "Allergies" in the selected searches 508). If the entry is critical, further emphasis may be displayed. For example, the exemplary screen displays pertain to a specialist's consideration of cardiac surgical procedures on a patient, so any patient medical record data element pertaining to anticoagulants must be reviewed. The entry for "Anticoagulants" in the recent reports 504 may be bolded and colored red, as an alert. Entries for queries that produced zero results may be displayed in half-tone or otherwise "grayed out."

Referring to FIG. 6a, a guidelines screen 600 may display information pertaining to generally accepted guidelines for a particular procedure, including aspects of a patient's medical history that must be reviewed prior to considering the procedure. The information may further include indications as to whether and how the patient conforms to the guidelines in light of the patient's medical history and current presentation. In some embodiments, the guidelines to be considered may be obtained through queries to the guideline databases 226. Guidelines retrieved from a database may be structured or unstructured, and may indicate the patient medical record data elements to be considered and the acceptable ranges for such data elements. In some embodiments, the retrieved guidelines may include one or more decision algorithms for determining whether an intervention is proper in light of a patient's characteristics. For example, guidelines for a cardiac surgical procedure may be established through collection of results from reported previous procedures. From the procedures, surgical risks in the presence of certain conditions are obtained, and the guidelines set in light of the risks. Thus, the decision algorithms may require indications as to whether or not the patient has each of the conditions. In other embodiments, the system may derive the decision algorithms from the retrieved guidelines. For example, the system may translate a guideline obtained from the medical literature into a set of numerical evaluation and Boolean steps to be executed by the system. Where guidelines and their associated decision algorithms are not patient-specific, the system may store the guidelines and decision algorithms after their first retrieval and/or generation, and apply them to any suitable patient.

The system employs either numerical or Boolean assessments of the results of conceptual search queries specified by the decision algorithms. For example, in the calculation of an estimate of surgical mortality, many guidelines may include the categorical question, "does the patient have a cardiac arrhythmia?" To address this question in the patient abstract generation, the system may use the conceptual query, "cardiac arrhythmia," which specifies terms and conditions that denote the positive, definite presence of this condition in a patient's record. As the application is executed, if this "cardiac arrhythmia" query returns a positive result, then the system can provisionally make an assertion that the patient has this condition and can display the supporting evidence for this to the specialist. The specialist may have the ability to review, and if need be, override the provisional assertion made by the system based on its conceptual search result. Once the assertion is finalized by the specialist, the system can then use the final state of the categorical assertion (e.g., the patient does or does not have a cardiac arrhythmia) in the subsequent calculation of surgical risk, where the calculation is specified by appropriate reference in the medical literature.

To achieve this, the present disclosure provides a system and method that is able to translate a binary representation of clinical criteria, such as a table of concepts and clinical scenarios to which appropriateness has been assigned, into a mathematical and hierarchical tree structure that provides an efficient system for clinical navigation to assign appropriateness for any given combination of clinical criteria. As a non-limiting example, FIG. 6b provides an example of one binary table 610 that reflects guidelines for the appropriate us of diagnostic catheterization. The table 610 is divided into a plurality of indications 612 that are further segregated by categories 614, 616, 618. The indications 612 and categories 614, 616, 618 are correlated with an appropriate use score 620 that is adjusted based on a determination of the clinical progress of the patient 622. Thus, to use the table 610, the clinician must scour the medical history of the patient to identify the historical information necessary to determine the correction indications 612, categories 614, 616, 618, and clinical progress of the patient 622, all so the clinician can arrive at an appropriateness score 620 that is further associated with a variety of additional indications 624. To further complicate the matter for clinicians, the table 610 illustrated in FIG. 6b is but one example of a guideline. Other guidelines may take a variety of other forms, require very-different information, and have very-different language or ultimate information for the clinician.

Figure 6C:
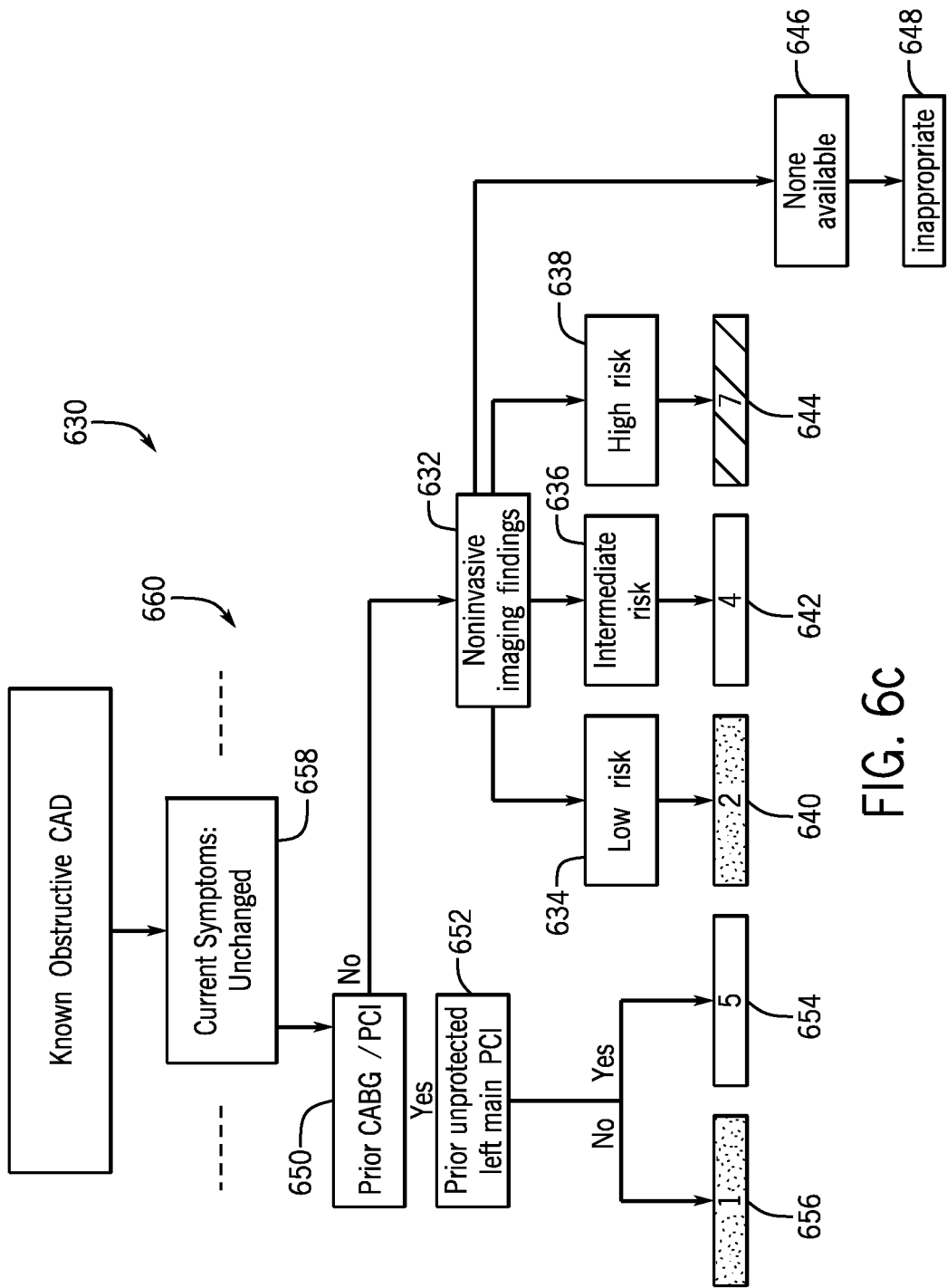
FIG. 6c is an example of a hierarchical tree structure built from the table of FIG. 6b.

Thus, as described above, the present disclosure provides a system and method that can translate information associated with guidelines into a more usable format to facilitate clinician interaction and decisions. For example, FIG. 6c provides one non-limiting example of a hierarchical tree structure 630 that may be automatically created from a guideline and utilized to facilitate clinical decision making. That is, in accordance with the present disclosure, the table 610 of FIG. 6b may be converted or translated into the hierarchical tree structure 630 of FIG. 6c. The conversion process may sort all categories or scenarios 614, 616, 618 and group all scenarios according to the associated appropriate use score 620. For example, the conversion process may seek to answer the question, "Has the patient had prior non-invasive cardiac imaging?" To this end, the grouping process takes all scenarios from the binary table with "non-invasive cardiac imaging" as a binary criterion at process block 632 of FIG. 6c and creates risk blocks 634, 636, 638 with associated color and number indications 640, 642, 644. To complete the possible branches of this portion of the tree 610, a "none available" block 646 and an associated "inappropriate" scenario 648 is created.

Precedence of groups is established by description in the medical literature. Working from that precedence, a further filtration of the tree is performed to avoid un-necessary testing of clinical criteria whose inputs and outputs are logically irrelevant for determination of a particular criterion node status. For example, from the literature, the determination of appropriateness for coronary intervention in cardiology may require knowledge and attestation of the patient's prior non-invasive imaging procedures (the clinical criterion, "Has the patient had prior non-invasive imaging"?); however, from the literature, this particular criterion is dependent in the tree to the criterion, "has the patient had a prior coronary intervention"? If the latter is true ("yes"), then the determination of prior cardiac imaging is irrelevant, according to the guideline literature and associated binary table. Thus, the system guides the calculation of appropriateness only using those criteria that are logically dependent (clinically relevant). With this in mind, the hierarchical tree structure 630 can continue to be built based on the binary guideline table 610 of FIG. 6*b*. Specifically, moving back from block 632, a Prior CABG/PCI decision block 650 is created. Based thereon, if there was prior CABG/PCI, the tree 630 is built to determine whether prior unprotected left main PCI exists at decision block 652 and, if so or if not, associated color and number indications 654 and 656 are provided.

This processing for building the hierarchical tree structure 630 continues until all parts of the guidelines are considered and reflected in the hierarchical tree structure 630 or determined to be not clinically relevant/logically dependent. Thus, in the illustrated example hierarchical tree structure 630, there would be additional branches 660 that are not illustrated in FIG. 6*c* for simplicity of illustration.

Additionally or alternatively, the guideline calculation may be driven not by reference to the medical literature, but rather by a regression analysis or machine learning algorithm based on actual stored outcomes recorded electronically by the system. In other words, the system may determine if concepts and factors present in a given patient's record were associated in prior clinical examples with certain clinical outcomes (such as death during surgery). In this embodiment, the system would be making association of particular concepts with increased or decreased risk of a particular clinical outcome based on reference to patient outcomes stored on the system, rather than by reference to medical literature guidelines.

In contrast to the clinical summary screen 500, which primarily displays information from the patient's medical history, the guidelines screen 600 may require a greater amount of specialist input because the needed information pertains largely to the patient's current condition to then guide the specialist or clinician to navigate the hierarchical tree structure. That is, the user makes an attestation (radio button selection) and then, in the background, the system calculates the appropriateness score for that particular part of the tree structure. Where the retrieved guidelines indicate that the specialist should manually provide a data element, rather than the system automatically providing it by performing queries, the text of the question may be displayed with a flag, such as an asterisk. Furthermore, some data elements may be provided by the system through queries but may require updating by the specialist due to the patient's presentation. The specialist may have the option to override a value for a data element first provided by the system, in which case an indicator that the system's value was overridden may appear (see "Symptomatic" and "Stenosis" in presentation 602).

The guidelines screen 600 may be organized according to the categories of patient data that should be considered for one or more of the potential interventions. The categories may include, without limitation: the patient's current presentation 602, including whether the patient is symptomatic and the types of symptoms that are relevant to the selected intervention; procedural risks 604 including any typical aspect that may present a procedural risk and whether the patient exhibits that aspect; medical therapy 606, including whether the patient has been prescribed any types of medications that may impact the risks of the intervention; and required questions 608 that list any other factors affecting the propriety of the intervention.

Referring to FIG. 7, a risks screen 700 may display one or more evaluations 705, 710 of risks to the patient of performing one or more of the interventions upon the patient, in light of the retrieved guidelines. Each evaluation may include a list of risk factors indicated by the guidelines. The system may automatically provide an indication for whether the risk factor is present in the patient's medical history by performing one or more queries of the patient's medical records for the relevant terms as described above. For example, the evaluation 705 for a carotid artery stenting ("CAS") procedure on the example patient carries factors that enhance the risk of stroke or death during the procedure—specifically, the patient's medical records indicate a prior stroke on Aug. 27, 2012, as well as previously reported heart fibrillation or flutter and previous ipsilateral CEA. The system provisionally indicates the presence of these risk factors and incorporates them into the assessment described below. In contrast, the example patient does not have any of the risk factors for carotid endarterectomy ("CEA"), as indicated by evaluation 710.

Figure 8:
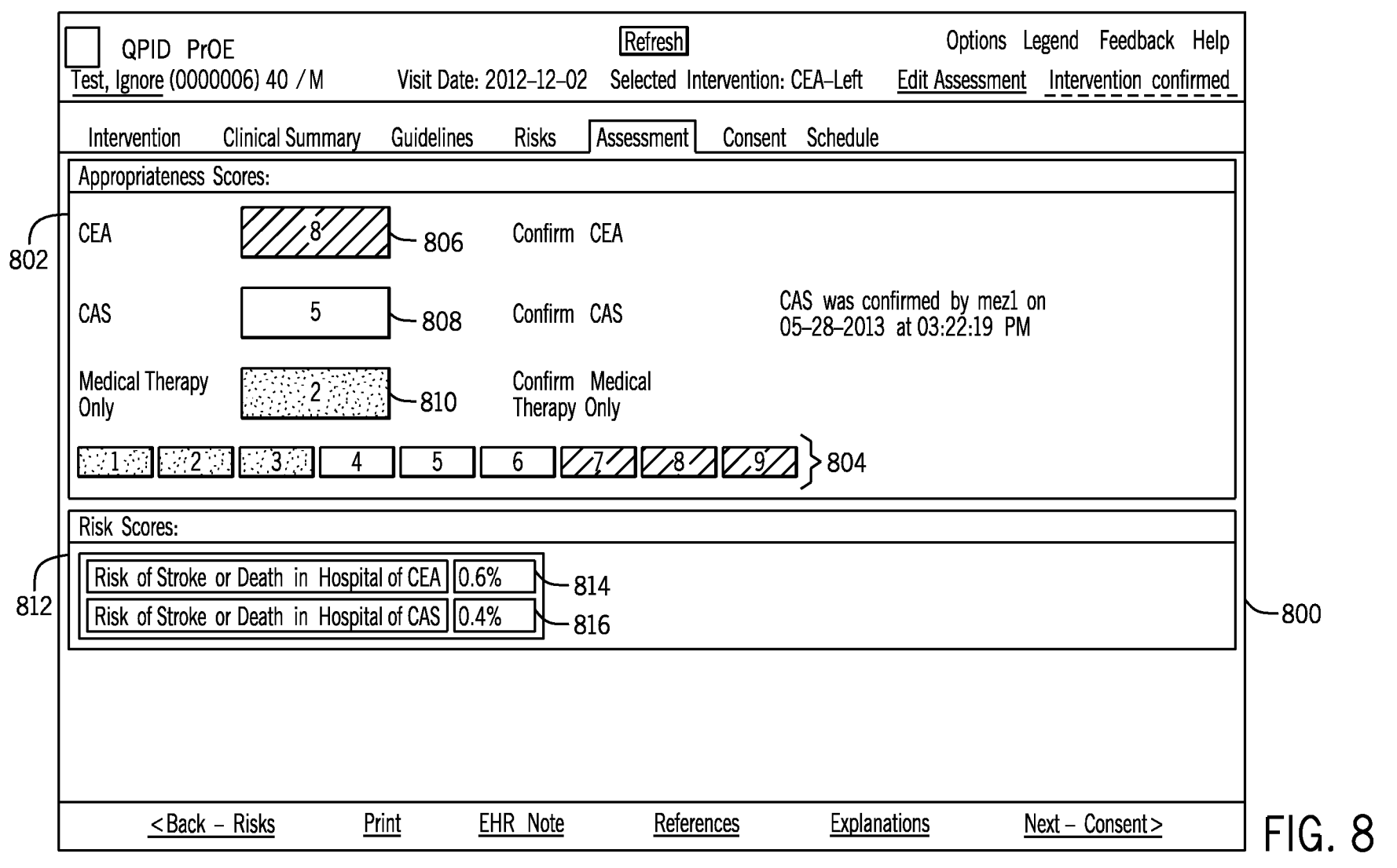

Referring to FIG. 8, an assessment screen 800 may display one or more assessments of the propriety of one or more of the potential interventions. The assessments may be based on the patient's medical history and current presentation in light of the guidelines and other medical information obtained from external sources 222. An assessment may include an appropriateness score 802. The appropriateness score 802 may include a scale, such as 9-position color-coded scale 804, of increasing propriety of the intervention. The propriety may be a function of the patient's medical history and current presentation in view of existing evidence that the intervention is or is not useful or effective for treating a patient having certain of the patient's characteristics. The appropriateness score 802 may include an indication 806, 808, 810 of where on the scale 804 each potential intervention falls.

An assessment may be a risk score 812. The risk score may be a scale or a percentage likelihood for a particular risk 814, 816. For example, the risk score 812 of FIG. 8 includes the risk 814 to the patient of stroke or death in the hospital if a CEA is performed, and the risk 816 of the same concern if a CAS is performed. Such risks 814, 816 may be calculated using algorithms published in the medical literature and retrieved from one or more external sources 222 and implemented by the system as described above. In particular, calculation of the risks may include the combination of categorical and numerical data according to algorithms derived and validated from prior clinical research.

Figure 9:
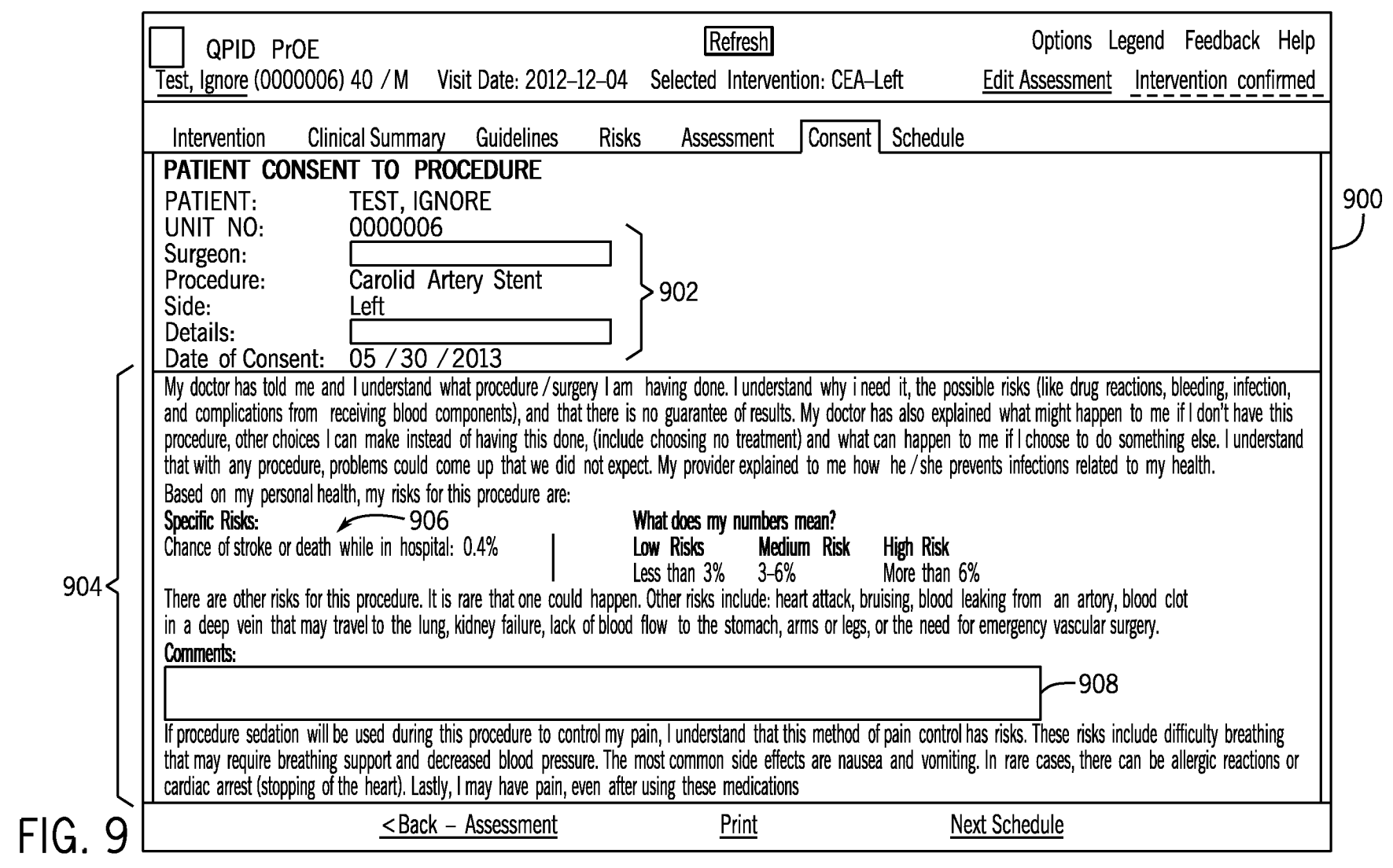

Referring to FIG. 9, the user interface may include a consent screen 900 for generating a patient consent form once an intervention has been selected. The patient consent screen 900 may include the patient's information 902 and the text 904 of the consent. The text 904 may include a statement 906 of the risks as determined by the system, and may further include a comment box 908 for the specialist to add any other text. The user interface can use the information entered into the consent screen 900 to generate the consent form and send it to a printer for obtaining the patient's signature. Alternatively, the user interface may present the consent form electronically for the patient's electronic signature.

Referring to FIG. 10, the user interface may include a schedule screen 1000 for generating a procedure scheduling request once the patient has consented to having the selected intervention performed. The schedule screen may include the patient's information, procedure information, urgency of the procedure, performing specialist, and any additional notes. The scheduling request may be transmitted to a scheduling department for scheduling, or the request may be processed immediately by the system to present an appointment schedule to the specialist.

Referring to FIG. 11, a medical history screen 1100 provides an alternative organizational view of the patient's medical history than the clinical summary screen 500. A records list 1102 may include categorized entries listed according to any suitable filter and sorting algorithm. For example, the records list 1102 may display, chronologically, the last 5-10 entries from the notes, studies, radiology, microbiology, pathology (no records in the example), and labs (no records in the example) categories. Similarly, a medical history table 1104 may include categorized entries that allow the specialist to access patient records by the biological system (in order from left: cardiovascular, pulmonary, gastrointestinal, genitourinary, immune system, neurological, hematological, and other (e.g. psych)) to which they pertain. An examination findings table 1106 may organize the results of previous examinations by name or category. A devices table 1108 may organize records that describe devices previously implanted or used in a procedure. A common workups table 1110 may organize the previous results of all or a subset of tests that are typically performed by certain types of physicians.

Optionally, the specialist may provide feedback to the system to indicate usefulness of any of the items displayed in the abstract 202. Feedback provided via the user interface may be used to alter the weights associated with term, concepts and/or data elements used to select the item, about which feedback has been provided. The adjustment can be made globally, so that changes to the weights are reflected through the ontology, regardless of the specialty for which a particular abstract is being generated. Alternatively, the feedback may be used to only adjust weights that are used in generating patient abstracts for the specialty for which the patient abstract was originally generated. This alteration may be done automatically, such as in response to each instance of feedback or in response to more than a predetermined number of instances of feedback on a single item. Optionally or alternatively, the feedback may be recorded and provided, such in a report, to a human administrator, who may then adjust the weights. If a sufficiently volume of negative feedback is generated, a system administrator may be notified, allowing the administrator to investigate the problem and determine whether the ontology, or its associated weights, requires adjustment.

Optionally, the amount of detail displayed for each item in the abstract 202 may be selected based upon a user selected parameter. In one embodiment, if the parameter indicates that the specialist 208 is an expert, less detail is displayed. However, if the parameter indicates that the specialist 208 is less experienced, more detail is displayed. The level of expertise of a particular specialist can be implemented as a multiplier assigned to the weights associated with the ontology for that specialty.

Although the abstract 202 has been described as being displayed on a computer screen, other embodiments of the present invention produce the abstract in printed form. Obviously, electronic links such as hyperlinks may not be invoked on a printed document; however, references to additional information may be included in a printed document, such as via footnotes.

As noted, the relationships among terms, concepts and data elements, including their weights, may be adjusted over time, such as in response to new medical knowledge. For example, ulcers were at one time thought to be related to stress, but they are now known to be an infectious disease. As a result of this new knowledge, associations and weights of associations among terms, concepts and data elements related to gastric ulcers and psychology may be changed, and such associations between ulcers and *Helicobacter pylori* infection may be created or adjusted.

Different specialists may interpret identical data in different ways. For example, fever may raise different issues in the minds of oncologists than in the minds of orthopedists. Optionally, the system includes a parameter that identifies the specialist's specialty and uses different weights, based upon the specialty, so as to include potentially different data items in the abstract.

Other uses of the disclosed systems and methods include scheduling intervention procedures, ensuring adherence to protocols for intervention procedures and preparing primary care physicians for patients attending office visits without referrals. In the latter case, the abstract is generated from the physician's schedule, not based upon an order.

Figure 12:
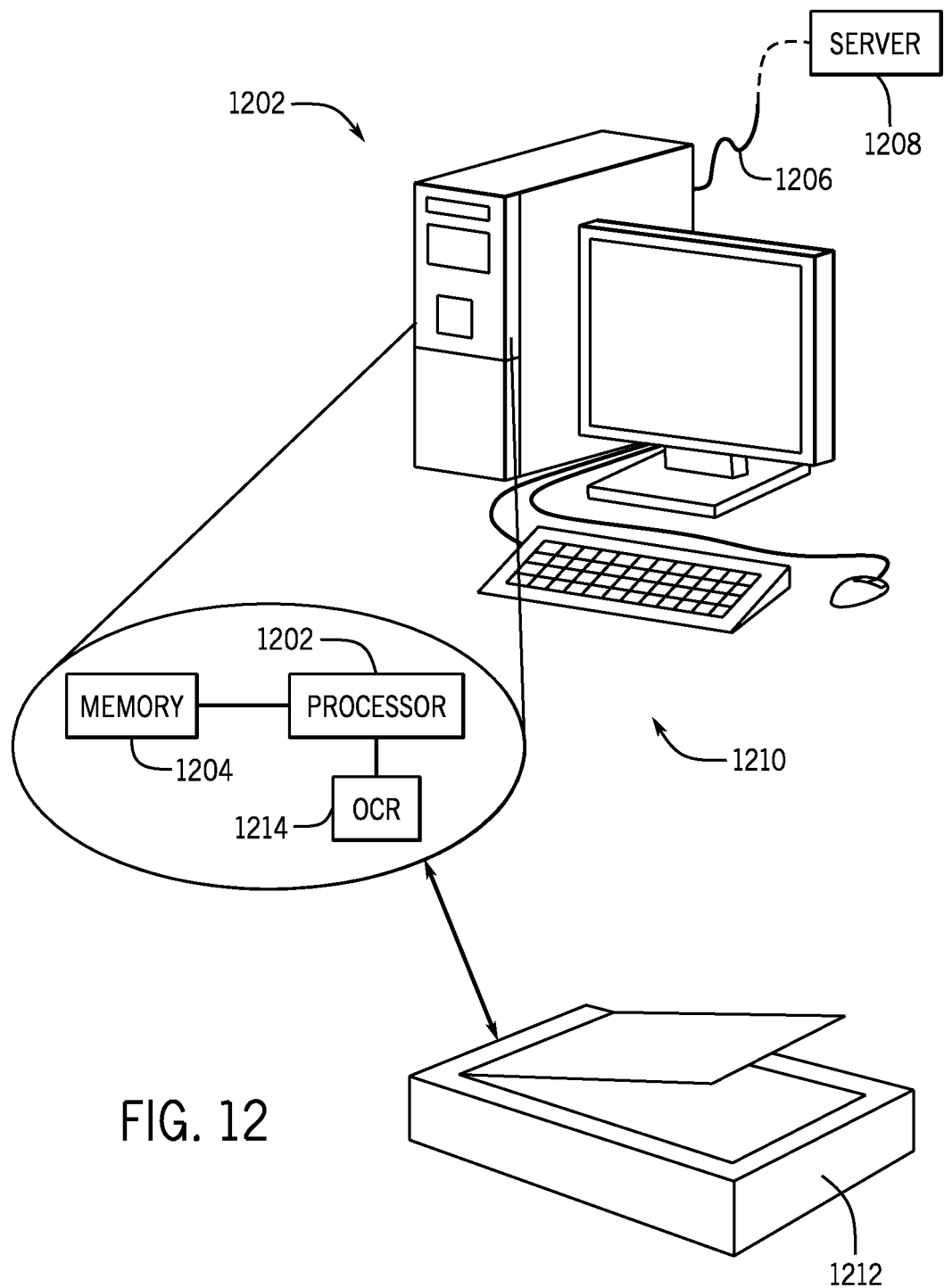
FIG. 12 is an schematic of a computer system that may be used to implement the systems of FIGS. 1-11 in accordance with the present disclosure.

FIG. 12 is an illustration of an example computer system that may be used to generate patient abstracts in accordance with the present disclosure. Computer system 1200 includes processor or processing unit 1202. Processor 1202 is controlled by instructions stored in memory 1204. Memory 1204 may be random access memory (RAM), read-only memory (ROM), flash memory or any other memory, or combination thereof, suitable for storing control software or other instructions and data. Computer 1200 includes communication connection 1206 for communicating with one or more external computer system such as servers, database, or other data stores that may contain a patient's medical record via an electronic communications network. Computer 1200 is also in communication with data storage or memory 1208 upon which an ontology, as described above, may be stored. In other implementations, though, the ontology can be stored on memory 1204. Computer 1200 is connected to user interface 1210 for displaying information to a user and receiving input (e.g., feedback) from the user. Some of the functions performed by the processors and databases have been described with reference to flowcharts in the present disclosure.

In some implementations, computer system 1200 may be in communication with scanner 1212. For example, when processing a medical order that was originally written by hand, scanner 1212 can scan an image of the medical order which can then be stored in memory 1204. After being stored in memory 1204, OCR system 1214 can then access memory 1204 can convert at least a portion of the image into machine-readable text data (e.g., ASCII strings) that can then be processed by processor 1202.

Figure 13:
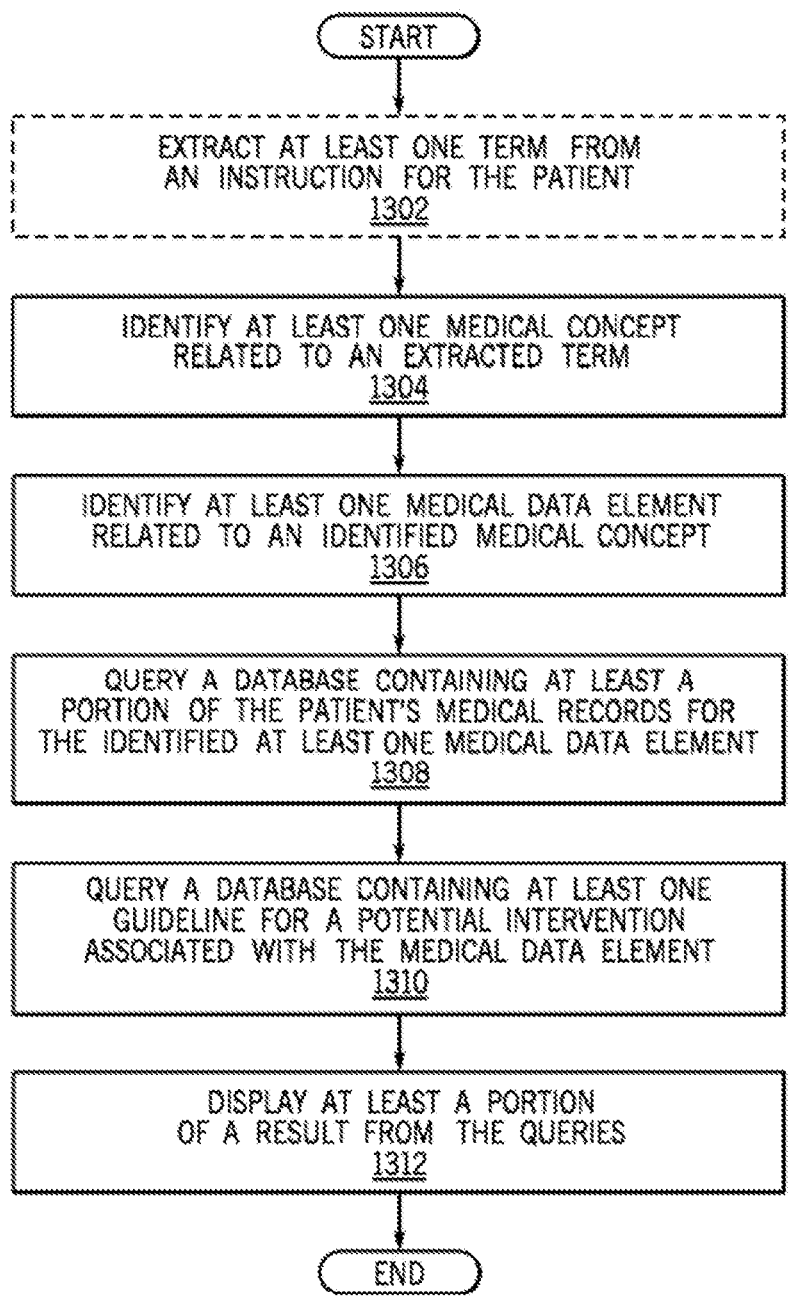
FIG. 13 is a flow chart setting forth the steps of one example method in accordance with the present invention that may be implemented by the computer system of FIG. 12.

FIG. 13 is an illustration of one example method that may be implemented by the computer system of FIG. 12 for generating a patient abstract and user interface according to the present disclosure. In step 1302, the system extracts at least one term from an instruction, such as an order, for the patient, if one is provided. The medical order can be received via a user interface, for example. In step 1304, the system identifies at least one medical concept related to an extracted term, and in step 1306 the system identifies at least one medical data element related to an identified medical concept. In step 1308 the system queries a database containing at least a portion of the patient's medical records for the identified at least one medical data element. In step 1310, the system queries a database containing at least one guideline for a potential intervention, as described above. In step 1312, the system displays at least a portion of a result from the queries.

Those of ordinary skill in the art should readily appreciate that functions, operations, decisions, etc. of all or a portion of each block, or a combination of blocks, of the flowcharts may be implemented as computer program instructions, software, hardware, firmware or combinations thereof. Those of ordinary skill in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various illustrative data structures, one skilled in the art will recognize that the system may be embodied using a variety of data structures. Furthermore, disclosed aspects, or portions of these aspects, may be combined in ways not specifically listed above. Accordingly, it is felt therefore that the scope of protection provided by this patent should not be viewed as limited by the above description, but rather should only be limited by the scope of the below claims.

The invention claimed is:

1. A system comprising:
a plurality of computer systems;
a database containing at least a portion of a medical record for a patient;
at least one external data source having information about at least one guideline for performing at least one intervention; and
a communications network coupling the plurality of computer systems, the database, and the at least one external data source together to facilitate communication therebetween,
such that at least one computer system of the plurality of computer systems is configured to:
obtain, via the communications network, the at least one guideline from the at least one external data source;
in real time, convert the at least one guideline into a set of data structures;
in real time, automatically build a hierarchical tree using the at least one guideline;
convert the hierarchical tree into an interactive user interface that, in response to user input, navigates between nodes of the hierarchical tree, wherein the interactive user interface includes at least one popup containing detailed information in response to an input cursor being placed over one or more of the nodes;
obtain a medical order for the patient from the database;
extract a first term from the medical order;
determine a first weight associated with a relationship between the first term and a candidate medical concept;
identify the candidate medical concept as a first medical concept in response to the first weight being greater than a first threshold;
determine a second weight associated with a relationship between the first medical concept and a candidate medical data element;
identifying the candidate medical concept as a first medical data element in response to the second weight being greater than a second threshold;
transmit an indicator of the first medical data element to the at least one external data source via the communications network, wherein the indicator of the first medical data element causes the at least one external data source to transmit the at least one guideline to the at least one computer system via the communications network;
query the database for the first medical data element in the medical record for the patient;
using (i) information from querying the database and (ii) navigation of the hierarchical tree, evaluate an appropriateness of the first medical concept or the medical order under the at least one guideline; and
visually indicate a result of evaluating the appropriateness of the first medical concept or the medical order.

2. The system of claim 1, wherein the first medical data element includes a characteristic of the patient.

3. The system of claim 1, wherein the at least one guideline is obtained from medical literature and the plurality of computer systems is further configured to automatically translate the at least one guideline into a set of numerical evaluation and Boolean steps forming the hierarchical tree.

4. The system of claim 3, wherein the at least one guideline is not patient-specific and at least one of the plurality of computer systems is configured to store the at least one guideline and the hierarchical tree for use with future patients.

5. The system of claim 1, wherein at least one of the plurality of computer systems is configured to generate a report indicating the result of evaluating the appropriateness of the first medical concept or the medical order in response to identification of the patient and without further input from a user of the system.

6. The system of claim 1, wherein the result of evaluating the appropriateness of the first medical concept or the medical order includes an appropriateness score or a risk score.

7. The system of claim 6, wherein the appropriateness score or the risk score is color coded.

8. A method comprising:
retrieving an ontology from at least one of an electronically-readable database and an electronically-readable memory, wherein the ontology defines relationships between a plurality of terms, a plurality of medical concepts, and a plurality of data elements;
in response to user selection of a patient, obtaining medical records of a patient;
extracting a first term from one or more entries in the medical records of the patient;
obtaining first information from the ontology related to the first term;
assigning a first weight to a relationship between the first term and a candidate medical concept according to the first information;
identifying the candidate medical concept as a first medical concept in response to the first weight being greater than a first threshold;
obtaining second information from the ontology related to the first medical concept;
assigning a second weight to a relationship between the first medical concept and a candidate medical data element according to the second information;
identifying the candidate medical data element as a first medical data element in response to the second weight being greater than a second threshold;
transmitting an indicator of the first medical data element to a medical record data store;
receiving medical record data associated with the first medical data element from the medical record data store;
transmitting the indicator of the first medical data element to an external data source over a network;
receiving, from the external data source via the network, one or more guidelines associated with the first medical data element, wherein each guideline of the one or more guidelines is applicable to one or more of a set of medical interventions;
in real time, converting the one or more guidelines received via the network into a set of data structures;
in real time, automatically building a hierarchical decision tree from the set of data structures;
displaying at least a portion of the medical record data associated with the first medical data element; and
converting the hierarchical decision tree into an interactive user interface that, in response to user input, navigates between nodes of the hierarchical decision tree,
wherein selected nodes of the hierarchical decision tree correspond to one or more of the set of medical interventions,
wherein the interactive user interface is configured to, in response to navigating to one of the selected nodes of the hierarchical decision tree, generate a visual indication related to one of the set of medical interventions corresponding to the one of the selected nodes, and
wherein the interactive user interface includes at least one popup containing detailed information in response to an input cursor being placed over one or more of the entries.

9. The method of claim 8, wherein:
identifying the first medical concept comprises identifying a plurality of medical concepts related to the first term, and
identifying the plurality of medical concepts related to the first term comprises comparing at least one of an average and a multiple of a plurality of weights associated with the plurality of medical concepts to the first threshold.

10. The method of claim 8, wherein the visual indication indicates whether one or more of the set of medical interventions is an appropriate procedure for the patient.

11. The method of claim 8, wherein an assessment corresponding to the visual indication comprises an appropriateness score.

12. The method of claim 11, wherein the assessment further comprises a risk score.

13. The method of claim 8, further comprising generating a report including an appropriateness score that is displayed in a color scale indicating an increasing level of appropriateness in a color coding.

14. The method of claim 8, further comprising providing access to a zero-click query presentation system that provides detailed information about displayed excerpts from the medical records.

15. A method comprising:
retrieving an ontology from at least one of an electronically-readable database and an electronically-readable memory, wherein the ontology defines relationships between a plurality of terms, a plurality of medical concepts, and a plurality of data elements;
in response to user selection of a patient, obtaining medical records of a patient;
extracting a first term from one or more entries in the medical records of the patient;
obtaining first information from the ontology related to the first term;
assigning a first weight to a relationship between the first term and a candidate medical concept according to the first information;
identifying the candidate medical concept as a first medical concept in response to the first weight being greater than a first threshold;
obtaining second information from the ontology related to the first medical concept;
assigning a second weight to a relationship between the first medical concept and a candidate medical data element according to the second information;
identifying the candidate medical data element as a first medical data element in response to the second weight being greater than a second threshold;
transmitting an indicator of the first medical data element to a medical record data store;
receiving medical record data associated with the first medical data element from the medical record data store;
transmitting the indicator of the first medical data element to an external data source over a network;
receiving, from the external data source via the network, one or more guidelines associated with the first medical data element, wherein each guideline of the one or more guidelines is applicable to one or more of a set of medical interventions;
in real time, converting the one or more guidelines received via the network into a set of data structures;
in real time, automatically building a hierarchical decision tree from the set of data structures;
displaying at least a portion of the medical record data associated with the first medical data element;
converting the hierarchical decision tree into an interactive user interface that, in response to user input, navigates between nodes of the hierarchical decision tree; and
providing access to a zero-click query presentation system that provides detailed information about displayed excerpts from the medical records, wherein selected nodes of the hierarchical decision tree correspond to one or more of the set of medical interventions, and wherein the interactive user interface is configured to, in response to navigating to one of the selected nodes of the hierarchical decision tree, generate a visual indication related to one of the set of medical interventions corresponding to the one of the selected nodes.

16. The method of claim 15, wherein:

identifying the first medical concept comprises identifying a plurality of medical concepts related to the first term, and identifying the plurality of medical concepts related to the first term comprises comparing at least one of an average and a multiple of a plurality of weights associated with the plurality of medical concepts to the first threshold.

17. The method of claim 15, wherein the visual indication indicates whether one or more of the set of medical interventions is an appropriate procedure for the patient.

18. The method of claim 15, wherein an assessment corresponding to the visual indication comprises an appropriateness score.

19. The method of claim 15, further comprising generating a report including an appropriateness score that is displayed in a color scale indicating an increasing level of appropriateness in a color coding.

20. A system comprising:

a plurality of computer systems;

a database containing at least a portion of a medical record for a patient;

at least one external data source having information about at least one guideline for performing at least one intervention; and a communications network coupling the plurality of computer systems, the database, and the at least one external data source together to facilitate communication therebetween, such that at least one computer system of the plurality of computer systems is configured to:

obtain, via the communications network, the at least one guideline from the at least one external data source;

in real time, convert the at least one guideline into a set of data structures;

in real time, automatically build a hierarchical tree using the at least one guideline;

convert the hierarchical tree into an interactive user interface that, in response to user input, navigates between nodes of the hierarchical tree;

obtain a medical order for the patient from the database;

extract a first term from the medical order;

determine a first weight associated with a relationship between the first term and a candidate medical concept;

identify the candidate medical concept as a first medical concept in response to the first weight being greater than a first threshold;

determine a second weight associated with a relationship between the first medical concept and a candidate medical data element;

identifying the candidate medical concept as a first medical data element in response to the second weight being greater than a second threshold;

transmit an indicator of the first medical data element to the at least one external data source via the communications network, wherein the indicator of the first medical data element causes the at least one external data source to transmit the at least one guideline to the at least one computer system via the communications network;

query the database for the first medical data element in the medical record for the patient;

using (i) information from querying the database and (ii) navigation of the hierarchical tree, evaluate an appropriateness of the first medical concept or the medical order under the at least one guideline;

visually indicate a result of evaluating the appropriateness of the first medical concept or the medical order; and provide access to a zero-click query presentation system that provides detailed information about displayed excerpts from the medical records.

* * * * *